United States Patent
Wang et al.

(10) Patent No.: US 10,815,523 B2
(45) Date of Patent: Oct. 27, 2020

(54) INDEXING BASED DEEP DNA SEQUENCING TO IDENTIFY RARE SEQUENCES

(71) Applicant: UNIVERSITY OF FLORIDA RESEARCH FOUNDATION, INCORPORATED, Gainesville, FL (US)

(72) Inventors: Gary P. Wang, Gainesville, FL (US); Chak Kar (Eric) Li, Oviedo, FL (US); Lin Liu, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 52 days.

(21) Appl. No.: 16/067,191

(22) PCT Filed: Dec. 23, 2016

(86) PCT No.: PCT/US2016/068464
§ 371 (c)(1),
(2) Date: Jun. 29, 2018

(87) PCT Pub. No.: WO2017/117034
PCT Pub. Date: Jul. 6, 2017

(65) Prior Publication Data
US 2019/0024150 A1    Jan. 24, 2019

Related U.S. Application Data

(60) Provisional application No. 62/272,857, filed on Dec. 30, 2015.

(51) Int. Cl.
*C12Q 1/6827*    (2018.01)
*C12Q 1/70*    (2006.01)
(Continued)

(52) U.S. Cl.
CPC ............. *C12Q 1/6827* (2013.01); *C12Q 1/68* (2013.01); *C12Q 1/6806* (2013.01);
(Continued)

(58) Field of Classification Search
None
See application file for complete search history.

(56) References Cited

U.S. PATENT DOCUMENTS

2010/0203497 A1    8/2010    Simen et al.
2012/0077682 A1    3/2012    Bowcock et al.
(Continued)

OTHER PUBLICATIONS

Kozich et al. Applied and Environmental Microbiology 2013; 79: 5112-5120 (Year: 2013).*
(Continued)

*Primary Examiner* — Angela M. Bertagna
(74) *Attorney, Agent, or Firm* — Saliwanchik, Lloyd & Eisenschenk

(57) ABSTRACT

The invention pertains to an assay that is capable of detecting a mutant polynucleotide in a plurality of polynucleotides. In one embodiment, the assay of the invention is capable of detecting one copy of a mutant polynucleotide in about 50,000 to about 100,000 copies of polynucleotides. The assay of the invention can be used to identify a mutant viral quasispecies or a mutant mRNA encoding an oncogenic protein from a tumor sample. The assay of the invention involves producing the single stranded complements of each of a plurality of polynucleotides containing the target sequence, wherein each of the single stranded complements contain a unique tag sequence and amplifying the single stranded complements by PCR using several sets of primers designed to introduce the sequences appropriate for a paired-end sequencing analysis of the amplified polynucleotides. The invention also pertains to kits for carrying out the assays of the invention.

10 Claims, 9 Drawing Sheets
(4 of 9 Drawing Sheet(s) Filed in Color)

Specification includes a Sequence Listing.

Schematic Figure for Single-Variant Sequencing

(51) Int. Cl.
*C12Q 1/68* (2018.01)
*C12Q 1/6806* (2018.01)
*C12Q 1/6874* (2018.01)

(52) U.S. Cl.
CPC ............. *C12Q 1/6874* (2013.01); *C12Q 1/70* (2013.01); *C12Q 2525/15* (2013.01); *C12Q 2525/155* (2013.01); *C12Q 2535/122* (2013.01); *C12Q 2563/179* (2013.01); *C12Q 2565/514* (2013.01)

(56) References Cited

U.S. PATENT DOCUMENTS

2014/0357499 A1 12/2014 Gordon et al.
2015/0087535 A1* 3/2015 Patel .................... C12Q 1/6858
506/4

OTHER PUBLICATIONS

Parameswaran et al. Nucleic Acids Research 2007; 35: e130. (Year: 2007).*
Picelli et al. Nature Protocols 2014; 9: 171-181. (Year: 2014).*
Kirst et al. PLoS ONE 2013; 8: e69698. (Year: 2013).*
Han et al. Nature Biotechnology 2014; 32: 684-692 + Online Methods. (Year: 2014).*
Becker, E. A. et al. "Experimental Analysis of Sources of Error in Evolutionary Studies Based on Roche/454 Pyrosequencing of Viral Genomes" *Genome Biology and Evolution*, Mar. 20, 2012, pp. 457-465, vol. 4, No. 4.
Herbold, C. W. et al. "A flexible and economical barcoding approach for highly multiplexed amplicon sequencing of diverse target genes" *Frontiers in Microbiology*, Jul. 16, 2015, pp. 1-8, vol. 6, No. 731.
Kirst, M. E. et al. "Deep Sequencing Analysis of HCV NS3 Resistance-Associated Variants and Mutation Linkage in Liver Transplant Recipients" *PLOS One*, Jul. 29, 2013, pp. 1-10, vol. 8, No. 7.
Loman, N. J. et al. "Performance comparison of benchtop high-throughput sequencing platforms" *Nature Biotechnology*, May 2012, pp. 434-439, vol. 30, No. 5., Online Methods pp. 1-2.
Illumina, "Illumina Sequencing Technology—Highest data accuracy, simple workflow, and a broad range of applications" retrieved from the Internet, https://www.illumina.com/documents/products/techspotlights/techsptlight_sequencing.pdf, Publication No. 770-2007-002, pp. 1-5., Oct. 11, 2010.
Van Den Hoecke, S. et al. "Analysis of the genetic diversity of influenza A viruses using next-generation DNA sequencing" *BMC Genomics*, 2015, pp. 1-23, vol. 16, No. 79.
Written Opinion in International Application No. PCT/US2016/068464, dated Mar. 29, 2017, pp. 1-7.

* cited by examiner

| | | \multicolumn{10}{c}{SVS Consensus} | \multicolumn{10}{c}{Raw Reads} |
| | Time from initial visit (yrs) | V 36 A G L M | F 43 S | T 54 A C I G S | V 55 A K I | Q 80 K L R | S 122 A G R | R 155 G K M T | A 156 S T V | D 168 AE HI KN PT VY | IV 170 A F T | V 36 A G L M | F 43 S | T 54 A C I G S | V 55 A K I | Q 80 K L R | S 122 A G R | R 155 G K M T | A 156 S T V | D 168 AE HI KN PT VY | IV 170 A F T |
|---|---|---|---|---|---|---|---|---|---|---|---|---|---|---|---|---|---|---|---|---|---|
| Subject 1 | 1.4 | – | – | – | – | ● | – | – | – | + | + | + | + | + | + | ● | + | + | + | + | + |
| | 4.6 | – | – | – | – | ● | – | – | – | – | – | + | + | + | + | ● | + | + | + | + | + |
| | 10.9 | – | – | – | – | ● | – | – | – | – | – | + | + | + | + | ● | + | + | + | + | + |
| Subject 2 | 0 | – | – | – | – | ● | – | – | – | – | – | + | + | + | + | ● | + | + | + | + | + |
| | 3.4 | – | – | – | – | ● | – | – | – | – | – | + | + | + | + | ● | + | + | + | + | + |
| | 4.7 | – | – | – | – | ● | – | – | – | – | – | + | + | + | + | ● | + | + | + | + | + |
| | 5.1 | – | – | – | – | ● | – | – | – | – | – | + | + | + | + | ● | + | + | + | + | + |
| | 5.9 | – | – | – | – | ● | – | – | – | – | – | + | + | + | + | ● | + | + | + | + | + |
| | 8.0 | – | – | – | – | ● | – | – | – | – | – | + | + | + | + | ● | + | + | + | + | + |
| | 9.5 | – | – | – | – | ● | – | – | – | – | – | + | + | + | + | ● | + | + | + | + | + |
| | 10.6 | – | – | – | – | ● | – | – | – | – | + | + | + | + | + | ● | + | + | + | + | + |
| Subject 3 | 0 | – | – | – | ● | – | – | – | – | – | – | + | + | + | ● | + | + | + | + | + | + |
| | 3.7 | – | – | – | ● | – | – | – | – | – | – | + | + | + | ● | + | + | + | + | + | + |
| | 5.1 | – | – | – | ● | – | – | + | – | – | – | + | + | + | ▲ | + | + | + | + | + | + |
| | 5.6 | – | – | – | ● | – | – | + | – | – | – | + | + | + | ▲ | + | + | + | + | + | + |
| Subject 4 | 0 | – | – | – | – | – | – | – | – | – | – | + | + | + | + | + | + | + | + | + | + |
| | 1.5 | – | – | – | – | – | – | – | – | – | – | + | + | + | + | + | + | + | + | + | + |
| | 6.3 | – | – | – | – | – | – | – | – | – | – | + | + | + | + | + | + | + | + | + | + |
| | 8.9 | – | – | – | – | – | – | – | – | – | – | + | + | + | + | + | + | + | + | + | + |
| Subject 5 | 0 | – | – | – | – | – | – | – | – | – | + | + | + | + | + | + | + | + | + | + | + |
| | 1.1 | – | – | – | – | – | – | – | – | – | – | + | + | + | + | + | + | + | + | + | + |
| | 2.1 | – | – | – | – | – | – | – | – | – | – | + | + | + | + | + | + | + | + | + | + |
| | 3.1 | – | – | – | – | – | – | – | + | – | – | + | + | + | + | + | + | + | + | + | + |
| | 3.6 | – | – | – | – | – | – | – | – | + | – | + | + | + | + | + | + | + | + | + | + |
| | 4.1 | – | – | – | – | – | – | + | – | – | – | + | + | + | + | + | + | + | + | + | + |
| | 4.6 | – | – | – | – | + | – | – | – | – | – | + | + | + | + | (+) | + | + | + | + | + |
| | 5.2 | – | – | – | – | – | – | – | – | – | – | + | + | + | + | + | + | + | + | + | + |
| | 6.3 | – | – | – | – | – | – | – | – | – | – | + | + | + | + | + | + | + | + | + | + |
| | 7.8 | – | – | – | – | – | – | – | – | – | + | + | + | + | + | + | + | + | + | + | (+) |
| | 9.5 | – | – | – | – | – | – | – | – | – | – | + | + | + | + | + | + | + | + | + | + |
| Subject 6 | 0 | – | – | – | – | ● | – | – | – | – | + | + | + | + | + | ● | + | + | + | + | + |
| | 2.0 | – | – | – | – | ● | – | – | – | – | + | + | + | + | + | ▲ | + | + | + | + | + |
| | 4.9 | – | – | – | – | ● | – | – | – | – | – | + | + | + | + | ● | + | + | + | + | + |

FIGURE 9

INDEXING BASED DEEP DNA SEQUENCING TO IDENTIFY RARE SEQUENCES

CROSS-REFERENCE TO RELATED APPLICATIONS

This application is the U.S. national stage application of International Patent Application No. PCT/US2016/068464, filed Dec. 23, 2016, which claims the benefit of U.S. Provisional Application Ser. No. 62/272,857, filed Dec. 30, 2015, the disclosures of which are hereby incorporated by reference in their entirety, including all figures, tables and amino acid or nucleic acid sequences.

The invention was made with government support under Grant No. A1077713 awarded by National Institutes of Health. The government has certain rights in the invention.

The Sequence Listing for this application is labeled "Seq-List.txt" which was created on Dec. 22, 2016 and is 9 KB. The entire content of the sequence listing is incorporated herein by reference in its entirety.

BACKGROUND OF THE INVENTION

Drug resistance to human immunodeficiency virus (HIV) is a major threat to achieving long-term viral suppression in $HIV^+$ individuals. Up to 16% of newly infected individuals acquire HIV with resistance to at least one of the major antiretroviral classes and incomplete viral suppression and virologic failure are often associated with drug resistance. Therefore, current DHHS guideline recommends drug resistance testing before beginning or changing antiretroviral therapy.

Current deep sequencing approaches encounter the uncertainties of the accuracy and sensitivity in quantifying human immunodeficiency virus 1 (HIV-1) and hepatitis C virus (HCV) minority populations. Therefore, identifying drug resistant quasispecies within the population of HIV-1 or HCV viruses infecting a patient is challenging.

BRIEF SUMMARY OF THE INVENTION

The invention provides an assay that is capable of detecting a mutant polynucleotide in a plurality of polynucleotides. In certain embodiments, the assay of the invention can identify one copy of a mutant polynucleotide in about 50,000 to about 100,000 copies of polynucleotides. The assay of the invention can be used to identify a mutant viral quasispecies, for example, a drug resistant viral quasispecies, within a sample of a virus obtained from a patient. The assay of the invention can also be used to detect a mutant mRNA encoding a mutant protein from a plurality of mRNAs. For example, the assay of the invention can be used to identify a mutant mRNA encoding a mutant protein in a sample of mRNAs isolated from a tumor to identify the oncogenic mutations in the tumor.

Accordingly, an embodiment of the invention provides an assay to identify, from a plurality of polynucleotides, a polynucleotide having a mutation within a target sequence.

The assay comprises the steps of:
a) producing a single stranded complement of a sequence corresponding to the target sequence in each of the plurality of polynucleotides containing the target sequence by one cycle of PCR using a plurality of first primers, wherein each of the plurality of the first primers comprises, from the 5' end:
  i) an outer PCR primer motif,
  ii) an inner PCR primer motif,
  iii) a tag comprising a sequence unique for each of the first primers, wherein the unique sequence comprises about 4-20 nucleotides, and
  iv) a 3' target sequence which has a sequence that corresponds to the sequence at the 3' end of the target sequence, wherein each of the single stranded complements of each of the plurality of polynucleotides produced in this step comprises, from the 5' end:
  i) the outer PCR primer motif,
  ii) the inner PCR primer motif,
  iii) the tag comprising a unique sequence of about 4-20 nucleotides,
  iv) the sequence corresponding to the target sequence, b) optionally, isolating the single stranded complements produced in step a), c) PCR amplifying the single stranded complements produced in step a) or isolated in step b) using a first primer set comprising an outer PCR primer and a first 5' target primer to produce multiple double stranded copies of each of the single stranded complements produced in step a), wherein the outer PCR primer has the sequence that corresponds to the outer PCR primer motif portion of the first primer and the first 5' target primer has the sequence that corresponds to the sequence at the 5' end of the target sequence, d) optionally, isolating the double stranded copies produced in step c), e) PCR amplifying the double stranded copies produced in step c) or purified in step d) using a second primer set comprising:
  i) a first barcode primer comprising, from the 5' end: a sequence corresponding to a 3' portion of a first sequencing primer, a first barcode and an inner PCR primer sequence, wherein the inner PCR primer sequence corresponds to the inner PCR primer motif portion of the first primer,
  ii) a second barcode primer comprising, from the 5' end: a sequence corresponding to a 3' portion of a second sequencing primer, a second barcode and a second 5' target sequence, wherein the second 5' target sequence corresponds to the portion of the target sequence that is at the 3' end of the sequence corresponding to the first 5' target primer, f) optionally, isolating the amplified double stranded copies produced in step e), g) PCR amplifying the double stranded copies produced in step e) or isolated in step f) using a third primer set comprising a first sequencing primer and a second sequencing primer, wherein the first sequencing primer has the sequence corresponding to the first paired-end sequencing primer and the second sequencing primer has the sequence corresponding to the second paired-end sequencing primer, h) optionally, isolating the amplified double stranded copies produced in step g), and i) subjecting the double stranded copies produced in step g) or purified in step h) to paired-end sequencing using the first paired-end sequencing primer and the second paired-end sequencing primer.

Certain embodiments of the invention also provide kits for carrying out the assays of the invention. The kits of the invention comprise specific primers necessary to carry out the assay of the invention, a computer software program designed to process the sequencing data obtained from the assay and optionally, materials that provide instructions to perform the assays of the invention.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 9. Identified genuine NS3 drug resistant mutations in HIV/HCV co-infection. Deduced amino acid (AA) substitutions in positions associated with resistance to NS3 protease inhibitors. The abundance of RAVs is shown as solid symbols (circles: AA frequency >99%, triangles: 95-99%), plus signs (+: AA frequency <1%, (+): AA frequency of 1-5%), or minus signs (−, RAVs not detected). Data after the sequencing correction is shown on the left and data for raw reads before the sequencing correction is shown on the right for comparison.

BRIEF DESCRIPTION OF THE SEQUENCES

Figure 1:
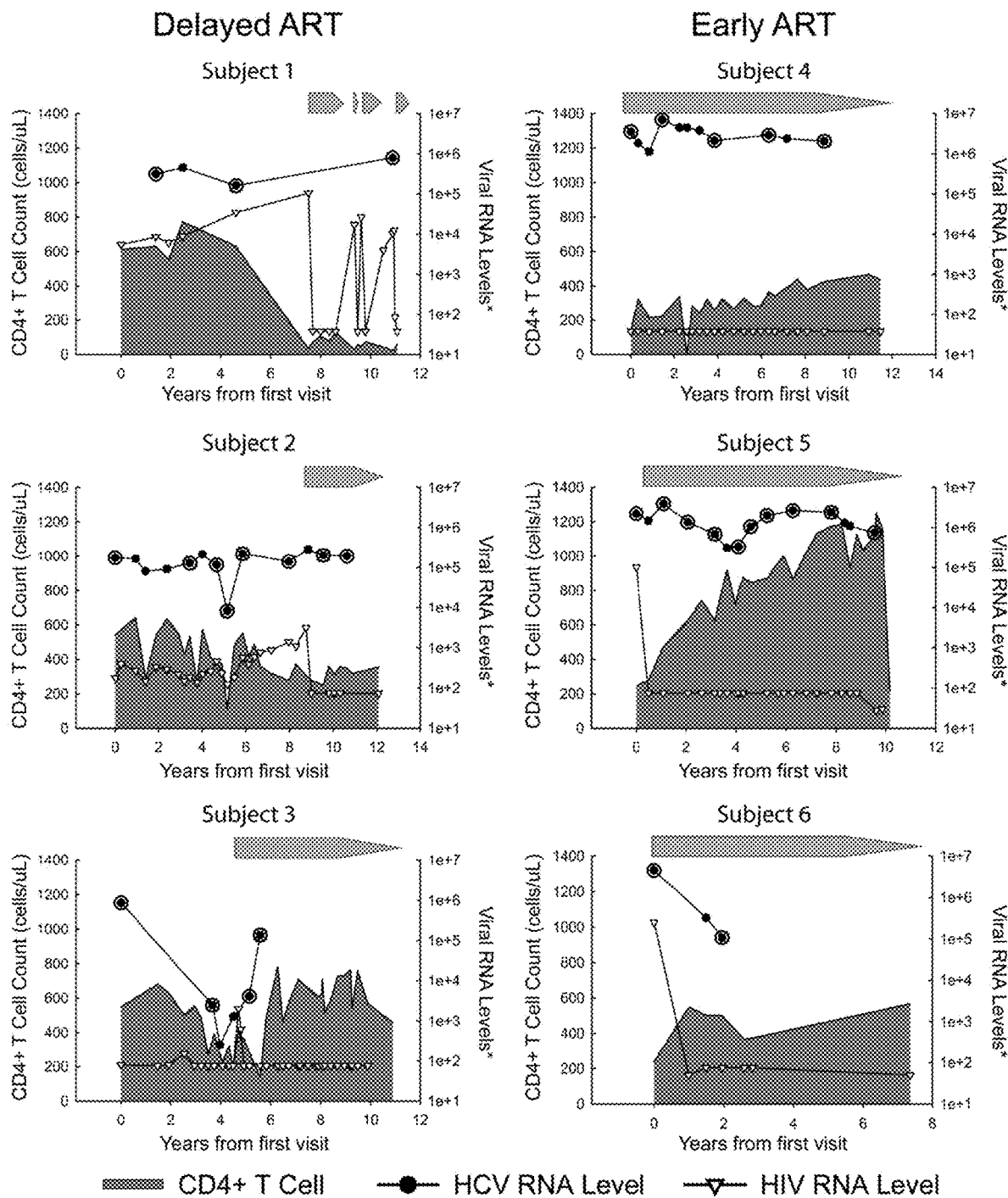
FIG. 1. Clinical laboratory parameters and duration of ART for HIV/HCV co-infected subjects analyzed in Example 3. For each subject, CD4+ T-cell counts are shown on the left vertical axis. HIV RNA (copies/mL) and HCV RNA (IU/mL) levels are shown on the right vertical axis. The gray arrow bar above each subject indicates the duration of ART. Serum samples analyzed for HCV gene sequencing are circled on the HCV RNA plot. Subjects 1-3 ("delayed ART" group) showed a gradual decline in CD4+ T-cell counts prior to initiation of ART. Subjects 4-6 ("early ART" group) received early ART and showed an increase in CD4+ T-cell counts over time.

| Primer Name | Primer Sequence | Purpose | SEQ ID NO: |
|---|---|---|---|
| HCV_BigE2R3_RTtag | TGACTCACGAGTCATCGACTGCAGGCAGATNNNNNNNNHVHBAGCAATAYACYGGGCCACA | E2 reverse transcription with tag | 1 |
| HCV_NS3_RTtag | TGACTCACGAGTCATCGACTGCAGGCAGATNNNNNNNNDHHHGACCTCATRGTTGTCTCTAG | NS3 reverse transcription with tag | 2 |
| FARCI_3MOD_OF | ATGGCATGGGATATGATGATGAACT | E2 nested PCR 5' first primer | 3 |
| HCV-NS3-3426F | ATYACRGCRTAYGCCCAGCA | NS3 nested PCR 5' first primer | 4 |
| ID-primer-OR | TGACTCACGAGTCATCGACT | E2 NS3 nested PCR outer PCR primer | 5 |
| HCV-E2-IF1 | CTACACGACGCTCTTCCGATCTCGTGTACAGCATRGCGTAYTTYTCCATGGT | E2 barcoding PCR primer | 6 |
| HCV-E2-IF2 | CTACACGACGCTCTTCCGATCTTGACTGACGCATRGCGTAYTTYTCCATGGT | E2 barcoding PCR primer | 7 |
| HCV-E2-IF3 | CTACACGACGCTCTTCCGATCTCTAGCTAGCATRGCGTAYTTYTCCATGGT | E2 barcoding PCR primer | 8 |
| HCV-E2-IF4 | CTACACGACGCTCTTCCGATCTACTGTCAGCATRGCGTAYTTYTCCATGGT | E2 barcoding PCR primer | 9 |
| HCV-E2-IF5 | CTACACGACGCTCTTCCGATCTGTAGTGGCATRGCGTAYTTYTCCATGGT | E2 barcoding PCR primer | 10 |
| HCV-E2-IF6 | CTACACGACGCTCTTCCGATCTCATGCGGCATRGCGTAYTTYTCCATGGT | E2 barcoding PCR primer | 11 |
| HCV-E2-IF7 | CTACACGACGCTCTTCCGATCTGCAGTGCATRGCGTAYTTYTCCATGGT | E2 barcoding PCR primer | 12 |
| HCV-E2-IF8 | CTACACGACGCTCTTCCGATCTTAGCTGCATRGCGTAYTTYTCCATGGT | E2 barcoding PCR primer | 13 |
| HCV-E2-IF9 | CTACACGACGCTCTTCCGATCTAGTAGCATRGCGTAYTTYTCCATGGT | E2 barcoding PCR primer | 14 |
| NS3-3613F-mod1 | CTACACGACGCTCTTCCGATCTCGTGATGAGTGGAGGGYGAGGTYCAGAT | NS3 barcoding PCR primer | 15 |
| NS3-3613F-mod2 | CTACACGACGCTCTTCCGATCTACATCGTGGTGGAGGGYGAGGTYCAGAT | NS3 barcoding PCR primer | 16 |
| NS3-3613F-mod3 | CTACACGACGCTCTTCCGATCTGCCTAAGGTGGAGGGYGAGGTYCAGAT | NS3 barcoding PCR primer | 17 |

-continued

| Primer Name | Primer Sequence | Purpose | SEQ ID NO: |
|---|---|---|---|
| NS3-3613F-mod4 | CTACACGACGCTCTTCCGATCTTGGTCACGTGGAGGGYGAGGTYCAGAT | NS3 barcoding PCR primer | 18 |
| NS3-3613F-mod5 | CTACACGACGCTCTTCCGATCTGACTGTGTGGAGGGYGAGGTYCAGAT | NS3 barcoding PCR primer | 19 |
| NS3-3613F-mod6 | CTACACGACGCTCTTCCGATCTCACTGTGTGGAGGGYGAGGTYCAGAT | NS3 barcoding PCR primer | 20 |
| NS3-3613F-mod7 | CTACACGACGCTCTTCCGATCTAGTGAGTGGAGGGYGAGGTYCAGAT | NS3 barcoding PCR primer | 21 |
| NS3-3613F-mod8 | CTACACGACGCTCTTCCGATCTTCAAGGTGGAGGGYGAGGTYCAGAT | NS3 barcoding PCR primer | 22 |
| NS3-3613F-mod9 | CTACACGACGCTCTTCCGATCTTCATGTGGAGGGYGAGGTYCAGAT | NS3 barcoding PCR primer | 23 |
| HCV-ID-IR1 | TGCTGAACCGCTCTTCCGATCTGTCAGCATCATCGACTGCAGGCAGAT | E2 NS3 barcoding PCR primer | 24 |
| HCV-ID-IR2 | TGCTGAACCGCTCTTCCGATCTTAGTCACGCATCGACTGCAGGCAGAT | E2 NS3 barcoding PCR primer | 25 |
| HCV-ID-IR3 | TGCTGAACCGCTCTTCCGATCTACGAGTGCCATCGACTGCAGGCAGAT | E2 NS3 barcoding PCR primer | 26 |
| HCV-ID-IR4 | TGCTGAACCGCTCTTCCGATCTGACCACTTCATCGACTGCAGGCAGAT | E2 NS3 barcoding PCR primer | 27 |
| HCV-ID-IR5 | TGCTGAACCGCTCTTCCGATCTCAGAGCTCATCGACTGCAGGCAGAT | E2 NS3 barcoding PCR primer | 28 |
| HCV-ID-IR6 | TGCTGAACCGCTCTTCCGATCTAGCATGTCATCGACTGCAGGCAGAT | E2 NS3 barcoding PCR primer | 29 |
| HCV-ID-IR7 | TGCTGAACCGCTCTTCCGATCTTATCGTGCATCGACTGCAGGCAGAT | E2 NS3 barcoding PCR primer | 30 |
| HCV-ID-IR8 | TGCTGAACCGCTCTTCCGATCTGTACATCCATCGACTGCAGGCAGAT | E2 NS3 barcoding PCR primer | 31 |
| HCV-ID-IR9 | TGCTGAACCGCTCTTCCGATCTATTGGCCATCGACTGCAGGCAGAT | E2 NS3 barcoding PCR primer | 32 |
| HCV-ID-IR10 | TGCTGAACCGCTCTTCCGATCTGATCTGCATCGACTGCAGGCAGAT | E2 NS3 barcoding PCR primer | 33 |
| HCV-ID-IR11 | TGCTGAACCGCTCTTCCGATCTCGACAACATCGACTGCAGGCAGAT | E2 NS3 barcoding PCR primer | 34 |
| HCV-ID-IR12 | TGCTGAACCGCTCTTCCGATCTTCGATACATCGACTGCAGGCAGAT | E2 NS3 barcoding PCR primer | 35 |
| HCV-ID-IR13 | TGCTGAACCGCTCTTCCGATCTCTGATCATCGACTGCAGGCAGAT | E2 NS3 barcoding PCR primer | 36 |

-continued

| Primer Name | Primer Sequence | Purpose | SEQ ID NO: |
|---|---|---|---|
| HCV-ID-IR14 | TGCTGAACCGCTCTTCCGATCT GTACGCATCGACTGCAGGCAGAT | E2 NS3 barcoding PCR primer | 37 |
| HCV-ID-IR15 | TGCTGAACCGCTCTTCCGATCT AAGCCATCGACTGCAGGCAGAT | E2 NS3 barcoding PCR primer | 38 |
| HCV-ID-IR16 | TGCTGAACCGCTCTTCCGATCTT ACCCATCGACTGCAGGCAGAT | E2 NS3 barcoding PCR primer | 39 |
| HCV-ID-IR17 | TGCTGAACCGCTCTTCCGATCT GTCTCATCGACTGCAGGCAGAT | E2 NS3 barcoding PCR primer | 40 |
| HCV-ID-IR18 | TGCTGAACCGCTCTTCCGATCT CTACCATCGACTGCAGGCAGAT | E2 NS3 barcoding PCR primer | 41 |
| PE-PCR-Primer-1.0 | AATGATACGGCGACCACCGAG ATCTACACTCTTTCCCTACACG ACGCTCTTCCGATCT | sequencing PCR primer | 42 |
| PE-PCR-Primer-2.0 | CAAGCAGAAGACGGCATACGA GATCGGTCTCGGCATTCCTGCT GAACCGCTCTTCCGATCT | sequencing PCR primer | 43 |

DETAILED DISCLOSURE OF THE INVENTION

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%). In the context of the lengths of polynucleotides where the terms "about" or "approximately" are used, these polynucleotides contain the stated number of bases or basepairs with a variation of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

When ranges are used herein, such as for the size of the polynucleotides, number of PCR cycles, the combinations and sub-combinations of the ranges (e.g., subranges within the disclosed range) and specific embodiments therein, are explicitly included.

"Subject" refers to an animal, such as a mammal, for example a human. The assays described herein can be useful in both humans and non-human animals. In some embodiments, the subject is a mammal (such as an animal model of disease), and in some embodiments, the subject is human. The terms "subject" and "patient" can be used interchangeably.

The invention provides an assay which provides the speed, accuracy and long read capability of the high-throughput paired-end sequencing technology, for example, Illumina MiSeq™ technology, and the random sequencing tag strategy. The assays of the invention remove biases and technical artifacts that obscure representations of mutations and minority variants. The assays of the invention can be applied to identify rare mutations or minority populations in a pool of genetic material. In certain embodiments, the invention provides an assay to accurately detect a polynucleotide containing a mutation in a target sequence from at least about 50,000 to about 100,000 polynucleotides containing the target sequence.

In one embodiment, the assays of the invention are used to accurately quantify minority populations of drug resistant virus in a population of viruses. In certain embodiments, the virus is a DNA virus of an RNA virus. Examples of DNA or RNA viruses are well known to a person of ordinary skill in the art and a person of ordinary skill in the art can design an assay to study any virus based on the description of the assays provided herein. In certain embodiments, the assay of the invention is used for quantitative detection of mutant HIV-1 or HCV viruses, for example, drug resistant HIV-1 or HCV mutant viruses. In a further embodiment, the assay of the invention is used for the detection of drug resistant mutations in a virus and to determine the impact of drug resistant mutations on viral suppression in response to a drug, which in turn can be used for rational selection of optimal antiviral therapy, for example, antiretroviral therapy.

In certain embodiments, the assay of the invention is used to identify a mutant gene in a culture of a bacterium, yeast, fungus. In one embodiment, the assay of the invention is used to identify a mutant gene in a population of cells, for example, cells obtained from a tissue culture or cells obtained from a tissue sample of a subject.

In another embodiment, the assay of the invention is used to identify a mutant mRNA encoding a mutant protein from a plurality of mRNAs. In one embodiment, the assay of the invention is used to identify a mutant mRNA encoding a mutant oncogenic protein in a sample of mRNA obtained from a tumor. In certain embodiments, mRNAs containing the target sequence can be isolated from the mixture of all mRNAs from a sample, for example, using the sequence specific isolation of mRNAs for an oncogene of interest from a preparation of mRNAs from a tumor sample. Techniques of isolating sequence specific mRNAs are well known in the art, for example, using a sequence specific binding agent to isolate mRNAs having a sequence of interest.

Accordingly, an embodiment of the invention provides an assay to identify, from a plurality of polynucleotides, a polynucleotide having a mutation within a target sequence.

The assay comprises the steps of:
a) producing a single stranded complement of a sequence corresponding to the target sequence in each of the plurality of polynucleotides containing the target sequence by one cycle of PCR using a plurality of first primers, wherein each of the plurality of the first primers comprises, from the 5' end:
  i) an outer PCR primer motif,
  ii) an inner PCR primer motif,
  iii) a tag comprising a sequence unique for each of the first primers, wherein the unique sequence comprises about 4-20 nucleotides, and
  iv) a 3' target sequence which has a sequence that corresponds to the sequence at the 3' end of the target sequence,
wherein each of the single stranded complements of each of the plurality of polynucleotides produced in this step comprises, from the 5' end:
  i) the outer PCR primer motif,
  ii) the inner PCR primer motif,
  iii) the tag comprising a unique sequence of about 4-20 nucleotides,
  iv) the sequence corresponding to the target sequence,
b) optionally, isolating the single stranded complements produced in step a),
c) PCR amplifying the single stranded complements produced in step a) or isolated in step b) using a first primer set comprising an outer PCR primer and a first 5' target primer to produce multiple double stranded copies of each of the single stranded complements produced in step a), wherein the outer PCR primer has the sequence that corresponds to the outer PCR primer motif portion of the first primer and the first 5' target primer has the sequence that corresponds to the sequence at the 5' end of the target sequence,
d) optionally, isolating the double stranded copies produced in step c),
e) PCR amplifying the double stranded copies produced in step c) or purified in step d) using a second primer set comprising:
  i) a first barcode primer comprising, from the 5' end: a sequence corresponding to a 3' portion of a first sequencing primer, a first barcode and an inner PCR primer sequence, wherein the inner PCR primer sequence corresponds to the inner PCR primer motif portion of the first primer,
  ii) a second barcode primer comprising, from the 5' end: a sequence corresponding to a 3' portion of a second sequencing primer, a second barcode and a second 5' target sequence, wherein the second 5' target sequence corresponds to the portion of the target sequence that is at the 3' end of the sequence corresponding to the first 5' target primer,
f) optionally, isolating the amplified double stranded copies produced in step e),
g) PCR amplifying the double stranded copies produced in step e) or isolated in step f) using a third primer set comprising a first sequencing primer and a second sequencing primer, wherein the first sequencing primer has the sequence corresponding to the first paired-end sequencing primer and the second sequencing primer has the sequence corresponding to the second paired-end sequencing primer,
h) optionally, isolating the amplified double stranded copies produced in step g), and
i) subjecting the double stranded copies produced in step g) or purified in step h) to paired-end sequencing using the first paired-end sequencing primer and the second paired-end sequencing primer. The outer PCR printer motif, the inner PCR primer motif, the 3' target sequence, the outer PCR primer sequence, the first 5' target primer, the inner PCR primer sequence, the sequence corresponding to the 3' portion of the first sequencing primer, the sequence corresponding to the 3' portion of the second sequencing primer, the first sequencing primer, and the second sequencing primer can, each, be about 15 nucleotides in length and the isolating in steps d), f) and h) can be performed by gel extraction.

For the purposes of this invention, "the target sequence" is a sequence of interest in which the mutations are to be identified according to the assays of the invention.

In certain embodiments, the target sequence is present in the single stranded polynucleotides, for example, single stranded viral RNA or mRNA. When the target sequence is present in the single stranded polynucleotides, the sequence of the target sequence is represented from 5' to 3' direction of the single stranded polynucleotides. As such, the 5' and the 3' ends of the target sequence are defined by the direction of the single stranded polynucleotides.

In certain embodiments, the target sequence is present in the double stranded polynucleotides, for example, a gene of interest in double stranded genomic DNA or RNA. When the target sequence is present in the double stranded polynucleotides, the sequence of the target sequence is represented from the 5' to 3' direction of the coding strand (sense strand) or the non-coding strand (anti-sense strand) of the double stranded polynucleotide. Various primers used in the assay can be designed based on the sequence of the coding strand or the non-coding strand of the double stranded polynucleotides. Accordingly, the 5' and the 3' ends of the target sequence are defined by the strand which is selected in a particular assay.

In certain embodiments, the target sequence is about 100 to about 2000 bps, about 300 to about 1800 bps, about 400 to about 1600 bps, about 600 to about 1400 bps, about 800 to about 1200 bps or about 1000 bps. In further embodiments, the target sequence is about 400 to about 800 bps, or about 600 bps.

The first 5' target primer has the sequence that corresponds to the sequence at the 5' end of the target sequence. Also, as noted above, the "3' target sequence" portion of the first primer corresponds to the sequence at the 3' end of the target sequence. Therefore, the 5' end of the target sequence is marked by the sequence corresponding to the first 5' target sequence and 3' end of the target sequence is marked by the sequence corresponding to the 3' target sequence.

The phrase "a first sequence corresponds to a second sequence" as used herein indicates that the first sequence contains a portion which overlaps with the second sequence. Therefore, the second sequence binds to the sequence which is reverse complementary to the first sequence and acts as a primer for the PCR extension of the polynucleotide containing the portion which is reverse complementary to the first sequence. The second sequence may have the same size or may be larger or smaller than the first sequence. If the second sequence is longer than the first sequence, the second sequence contains extra nucleotides only on the 5' end of the first sequence, i.e., the second sequence will have a 5' overhang when the second sequence binds to the sequence which is reverse complementary to the first sequence. If the second sequence is shorter than the first sequence, it can be entirely encompassed by the first sequence or it can have an overlapping portion with the first sequence and extra nucleotides at the 5' end of the first sequence.

The description of sequence in terms of "corresponding to" indicates that a primer designed for use in the later steps of the assays of the invention contains a portion which overlaps with the sequence incorporated in to the amplicons produced during the earlier PCR steps of the assay. For example, when the outer PCR primer motif is incorporated in to the single stranded complement corresponding to the target sequence, the outer PCR primer has the sequence that contains a portion which overlaps with the outer PCR primer motif portion of the first primer and is able to PCR amplify the polynucleotide which is reverse complementary to the single stranded complement.

A person of ordinary skill in the art will appreciate that when the outer PCR primer has the sequence that contains a portion which overlaps with the outer PCR primer motif portion of the first primer, to PCR amplify the target sequence from the single stranded complement, the first 5' target primer must have the sequence that contains a portion which is reverse complementary to an appropriate portion of the single stranded complement produced in step a) described above. The principle of identical and reverse complementary primer pairs described herein is applicable to all the steps of the invention where PCR primers are designed based on the sequences incorporated in to PCR amplicons via the primers used in earlier PCR reactions. A person of ordinary skill in the art can appropriately design various PCR primers used in the assays of the invention.

When the polynucleotides analyzed according to the assay of the invention are RNAs, for example, mRNAs or genomic RNA from a virus, the first step of producing a single stranded complement of each of the plurality of RNAs containing the target sequence is carried out by a PCR using a reverse transcriptase enzyme. When the polynucleotides analyzed according to the assay of the invention are DNAs, for example, genomic DNA from a virus, bacterium, yeast, fungus or a human, the first step of producing a single stranded complement of each of the plurality of DNAs containing the target sequence is carried out by a PCR using a DNA polymerase.

A high fidelity polymerase is used in the first step of the invention (step a) as described above) because any errors in the first step will be copied during the subsequent PCR amplifications. Therefore, maintaining a high fidelity of amplification in the first step facilitates accurate identification of the mutants. Non-limiting examples of the high fidelity DNA polymerases include Platinum™ Taq DNA Polymerase (ThermoFisher Scientific) and Phusion™ High-Fidelity DNA Polymerase (New England Biolabs). Non-limiting examples of the high fidelity reverse transcriptase are AccuScript Hi-Fi Reverse Transcriptase™ (Agilent Technologies) and PrimeScript™ Reverse Transcriptase (Clontech). Additional examples of the high fidelity DNA polymerases and high fidelity reverse transcriptases are well known to a person of ordinary skill in the art and such embodiments are within the purview of the invention.

The first step of the assay of the invention (step a) described above) comprises incorporating the unique tag to the single stranded complements comprising the target sequence is referred to herein as "the tagging step".

Tagging step comprises subjecting a reaction mixture to one cycle of PCR amplification, wherein the reaction mixture comprises, target polynucleotides in which the mutants are to be identified and the plurality of the first primers. The reaction mixture in the tagging step also contains other reagents necessary for the PCR amplification, for example, an appropriate buffer, a polymerase enzyme, dNTPs, cofactors and salts necessary for the polymerase enzyme. Additional reagents used in the PCR reaction are well known to a person of ordinary skill in the art and such embodiments are within the purview of the invention.

Each of the plurality of the first primers used for the tagging step comprises, from the 5' end:
  i) an outer PCR primer motif,
  ii) an inner PCR primer motif,
  iii) a tag comprising a sequence unique for each of the first primers, wherein the unique sequence comprises about 4-20 nucleotides, and
  iv) a 3' target sequence which has a sequence that corresponds to the sequence at the 3' end of the target sequence.

Figure 6:
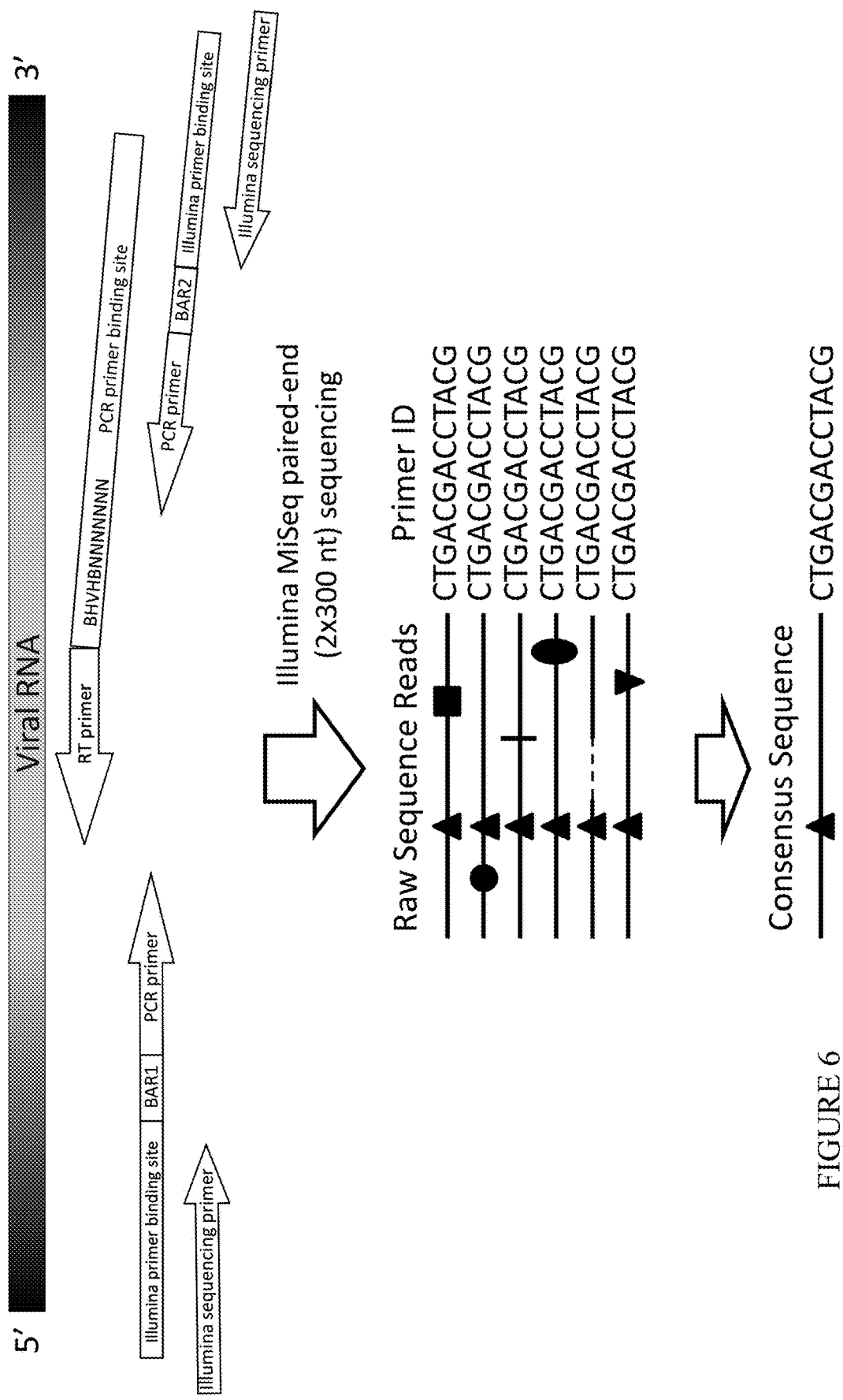
FIG. 6. Analysis of variants in HCV RNA. HCV RNA was amplified in a reverse transcription reaction using a primer that contains a random, non-binding sequence tag (SEQ ID NO: 44). Following reverse transcription, each cDNA molecule was labeled with a unique tag. This was followed by a nested PCR reaction and a third round PCR that adds the Illumina sequencing primer. Paired-end sequencing at 2×300 bases is then performed on a MiSeq™ Benchtop Sequencer (Illumina). Paired-end reads are stitched into one complete read using overlapping sequences. A consensus sequence is formed by clustering reads that have identical tags. Using this procedure, each consensus sequence represents the actual sequence of the initial RNA template. Technical artifacts such as allelic skewing, template resampling, and errors from PCR amplification and sequencing are corrected.

The outer PCR primer motif and the inner PCR primer motif portions of the first primer when incorporated in to the single stranded complement of the target sequence provide primer binding sites for the downstream PCR amplification steps (FIG. 6). The outer PCR primer motif and the inner PCR primer motifs are each about ten to 25 nucleotides, about 12 to 20 nucleotides, or about 15 nucleotides.

The tag comprising a sequence unique for each of the first primers is used to "uniquely tag" each of the single stranded complements produced from the plurality of polynucleotides. Therefore, the polynucleotides sequenced during the last step of paired-end DNA sequencing can be clustered together based on the presence of the unique tag sequence because once the unique tag is incorporated in the single stranded complement of the target sequence, the unique tag is replicated during each of the subsequent amplification steps and becomes a part of the resulting polynucleotides.

In certain embodiments, the tag is about four to about 20 nucleotides in length. Based on the four possible nucleotides (A, T, G or C) in each position of the tag, the number of possible random sequences that can be designed for the tag having "x" number of nucleotides can be calculated based on the following formula:

Number of random sequences=$4^x$

Therefore, the number of random sequences produced for tags having different lengths is show in Table 1 below.

TABLE 1

| Number of nucleotides in the tag | Total number of possible random sequences |
|---|---|
| 4 | 256 |
| 5 | 1,024 |
| 6 | 4,096 |
| 7 | 16,384 |
| 8 | 65,536 |
| 9 | 262,144 |
| 10 | 1,048,576 |
| 11 | 4,194,304 |
| 12 | 16,777,216 |
| 13 | 67,108,864 |
| 14 | 268,435,456 |
| 15 | 1,073,741,824 |
| 16 | 4,294,967,296 |
| 17 | 17,179,869,184 |
| 18 | 68,719,476,736 |
| 19 | 274,877,906,944 |
| 20 | 1,099,511,627,776 |

As evident from the table, a large number of unique tags can be designed with sequences of various lengths. In a preferred embodiment, the tag comprises about eight to about 15, about 9 to about fourteen, about ten to about 13, about 11 to about 12 or about 12 nucleotides. A tag of 12 nucleotides provides a possible 16,777,216 random sequences.

From the random sequences obtained from the tags of various lengths, the sequences that are complementary or identical to the sequences which may be present in the polynucleotides analyzed in the assay of the invention are removed. For example, in one embodiment, a 12-mer tag is used to identify a viral variant in a sample of viral RNA isolated from a subject. The viral RNA typically contains a mixture of viral quasispecies that contain closely related but not identical copies of RNA. The sequences of the random tags designed from the 12-mer are compared to the sequence of the viral RNA and the random 12-mer sequences that are reverse complementary to or identical to the viral RNA are excluded from the tag sequences.

The longer the tag, the less likely it is that a random 12-mer sequence may be present in the polynucleotides of interest. In certain embodiments, the additional restrictions are used when designing the tag sequences. The additional restrictions can be designed to avoid producing a tag which is identical to or complementary to the polynucleotides analyzed according to the assay of the invention.

An example of such additional restrictions on random tag sequences to avoid sequences that may be complementary to an HCV viral RNA is shown below:

BHVHBNINNNNNN, wherein B is A, C or G but not T; H is A, C or T but not G; and V is A, C or G but not T.

Such additional restrictions limit the possible number of random sequences that can be generated for a given length of tags.

The number of unique first primers added in the reaction mixture for this step is substantially higher than the number of polynucleotides present in the reaction mixture. For example, in certain embodiments, the number of unique first primers is about 10 to about 500 times, about 200 to about 400 times, or about 300 times the number of polynucleotides present in the reaction mixture. The large excess of the unique first primers compared to the number of polynucleotides present in the reaction mixture makes it less likely that two different polynucleotides would incorporate two first primers having an identical tag.

In one embodiment, about 50,000 to about 100,000 copies of a viral genomic RNA are added in a reaction mixture containing about 10 million to about 20 million first primers. In another embodiment, about 50,000 to about 100,000 copies of the mRNA of interest are added in a reaction mixture containing about 10 million to about 20 million first primers.

The "3' target sequence" portion of the first primer corresponds to the sequence at the 3' end of the target sequence. Therefore, the 3' target sequence marks the 3' end of the target sequence. The 3' target sequence is the only portion of the first primer that corresponds to the target sequence. Therefore, during the first step of producing the single stranded complement of each of the plurality of nucleotides containing the target sequence, the 3' target sequence binds to the corresponding portion at the 3' end of the target sequence.

As such, during the first step, the polymerase, for example, reverse polymerase if the polynucleotides are RNAs or DNA polymerase if the polynucleotides are DNAs, synthesizes the single stranded complement of each of the plurality of nucleotides, wherein each of the single stranded complements produced at the end of the reaction comprise, from the 3' end:
  i) the outer PCR primer motif,
  ii) the inner PCR primer motif,
  iii) the tag comprising a unique sequence of about 4-20 nucleotides,
  iv) the sequence corresponding to the target sequence.

Only one PCR amplification cycle is carried out in this step thereby producing only one copy of each of the plurality of polynucleotides. The conditions appropriate for the PCR cycle depend on the denaturation temperatures of the primers and optimal temperature for the polymerase enzyme used in this step. Designing proper PCR cycles based on the primer sequences and the polymerase is well known to a person of ordinary skill in the art.

The amplification cycle in the tagging step is conducted to ensure that the single stranded complement produced in this reaction encompasses the target sequence in its entirety. Therefore, if the target sequence is about 1 kb and the polymerase enzyme used in this reaction synthesizes at the rate of 1 kb/minute, the tagging step PCR reaction is carried out for at least about 2 to 3 minutes to ensure that 1 kb target sequence is synthesized in its entirety. Additional portion of the templates beyond the target sequence may be incorporated in to the single stranded complement of the target sequence; however, these sequences are not amplified during the subsequent PCR cycles because of the primer designs of the first and the second 5' target primers.

In certain embodiments, the single stranded complements produced in the tagging step are isolated and purified from the plurality of polynucleotides and the excess primers used in the tagging step. For example, when the plurality of polynucleotides are RNAs and the single stranded complements produced in the tagging step are DNAs, the plurality of polynucleotides can be digested using an RNAase enzyme thereby leaving the single stranded complementary DNA intact for further analysis. Additional techniques of isolating the single stranded complements produced in the tagging step are well known to a person of ordinary skill in the art and such embodiments are within the purview of the invention. The step of isolating the single stranded complements produced in the tagging step is optional.

The assay of the invention further comprises PCR amplifying the single stranded complements comprising the target sequence produced in the tagging step to produce double stranded copies of the single stranded complements. This step of amplifying the single stranded complements is performed using a first primer set comprising an outer PCR primer and a first 5' target primer to produce multiple double stranded copies of each of the single stranded complements produced in the tagging step. This step is referred to herein as "the nested PCR step".

The first 5' target primer and the outer PCR primer have lengths of about ten to 25 nucleotides, about 12 to 20 nucleotides, or about 15 nucleotides.

The outer PCR primer has the sequence that corresponds to the outer PCR primer motif portion of the first primer and the first 5' target primer has the sequence that corresponds to the sequence at the 5' end of the target sequence. The outer PCR primer has the sequence that contains a portion which overlaps with the outer PCR primer motif and the first 5' target primer has the sequence that contains a portion which is reverse complementary to an appropriate portion of the single stranded complement produced in the tagging step (FIG. 6). According, during the first amplification cycle of the nested PCR step, the first 5' target primer binds to the single stranded complements produced in the tagging step and is able to act as a primer for PCR extension of the single stranded complements. Consequently, using the first 5' target primer, the polymerase synthesizes a double stranded DNA comprising the single stranded complements produced in the tagging step and the strand complementary to the single stranded complements, including, the portions complementary to the inner PCR primer sequence, the tag sequence and the outer PCR primer sequence. During the denaturation phase of the second cycle of the PCR amplification in the nested PCR step, the single stranded complements produced in the tagging step are separated from the complementary strands produced in the first cycle of the nested PCR step. During the second amplification phase of the nested PCR step, the first 5' target primer binds to the corresponding sequence on the single stranded complements produced in the tagging step and denatured during the denaturation phase; whereas, the outer PCR primer binds to the corresponding reverse complementary sequence present in the strand synthesized during the first amplification phase of the first cycle of the nested PCR step. At the end of the second cycle of the nested PCR step, two double stranded polynucleotides, both containing the copies of the target sequence as well as the sequence corresponding to the outer PCR primer motif, the inner PCR primer motif and the tag sequence, are produced.

During the subsequent PCR cycles of the nested PCR step the double stranded polynucleotides are amplified to produce a large number of copies of each of the polynucleotides originally added in the reaction mixture during the tagging step. In a preferred embodiment, about 20 to about 35 PCR cycles are performed in the nested PCR step. The conditions appropriate for the PCR cycles during the nested PCR step depend on the denaturation temperatures of the primers and the polymerase enzyme used in the nested PCR step. Designing the proper conditions for the PCR cycles based on the primer sequences and the polymerase is well known to a person of ordinary skill in the art.

In certain embodiments, the double stranded polynucleotides produced in the nested PCR step are purified from the reagents used in the nested PCR step.

In the next step of the invention, the double stranded polynucleotides produced in the nested PCR step are further PCR amplified using a second primer set comprising:
  i) a first barcode primer comprising, from the 5' end: a sequence corresponding to a 3' portion of a first sequencing primer, a first barcode and an inner PCR primer sequence, wherein the inner PCR primer sequence corresponds to the inner PCR primer motif portion of the first primer,
  ii) a second barcode primer comprising, from the 5' end: a sequence corresponding to a 3' portion of a second sequencing primer, a second barcode and a second 5' target sequence, wherein the second 5' target sequence corresponds to the portion of the target sequence that is at the 3' end of the sequence corresponding to the first 5' target primer.

Since this step of the assay of the invention introduces barcodes in to amplified double stranded DNA products, this step is referred to as "the barcoding step".

The sequence corresponding to the 3' portions of the first and the second sequencing primers, the second 5' target sequence and the inner PCR primer have lengths of about ten to 25 nucleotides, about 12 to 20 nucleotides, or about 15 nucleotides.

During the first PCR cycle of the barcoding step, the denaturation phase of the PCR cycles produces the DNA strands that correspond to the single stranded complements produced in the tagging step and the DNA strands that are complementary to the single stranded complements produced in the tagging step.

In one embodiment, during the amplification phases of the PCR cycles in this step, the second barcode primer binds to the DNA strands that correspond to the single stranded complements produced in the tagging step; whereas, the first barcode primer binds to the strands synthesized in the nested PCR step and that are complementary to the single stranded complements produced in the tagging step. During the first PCR cycle of this step of the invention, the first and the second barcodes as well as the sequences corresponding to the 3' portions of the first and the second sequencing primers get incorporated in to the resulting double stranded polynucleotides. These double stranded polynucleotides are amplified in the subsequent PCR cycles.

The first and the second barcodes comprise about four to 12 nucleotides, preferably, about six to ten nucleotides, and even more preferably, about eight nucleotides. The first and the second barcodes have different sequences from each other. In one embodiment, all copies of the first barcode primer contain the same first barcode and all copies of the second barcode primer contain the same second barcode. In another embodiment, each of the first barcode primer contains a first barcode selected from about five to ten options for the first barcode sequence and each of the second barcode primer contains a second barcode selected from about five to ten options for the second barcode sequence.

The sequences of the first and the second barcodes are identified during the data analysis step of the invention and are used to align the sequence reads where the barcode sequences are used to determine the boundaries of the amplicons produced in the barcoding step.

The subsequent PCR cycles of this step produces multiple copies of double stranded polynucleotides, each containing:
  one strand comprising, from the 5' end, the sequence corresponding to:

i) the 3' portion of the first sequencing primer,
ii) the first barcode,
iii) the unique tag,
iv) the target sequence,
v) the second barcode, and
vi) the sequence corresponding to the 3' portion of the second sequencing primer; and one strand comprising, from the 5' end, the sequence corresponding to:
i) the 3' portion of the second sequencing primer,
ii) the second barcode,
iii) the target sequence,
iv) the unique tag,
v) the first barcode, and
vi) the 3' portion of the first sequencing primer.

For schematic representations of these descriptions, see FIG. 6.

In one embodiment of the invention, the sequences of the first 5' target primer and the second 5' target primer overlap with each other. In another embodiment the first 5' target primer and the second 5' target primer have identical sequences, i.e., they both bind to the same site on the single stranded complements produced in the tagging step.

In one embodiment of the invention, only an outer primer motif is used in the first primers and the primer containing a sequence corresponding to only the outer primer motif is used in the subsequent PCR amplifications in the claimed assay.

As such, at the end of the barcoding step, the assay of the invention provides a large number of double stranded polynucleotides each of which contain a strand containing the target sequence and the unique tag flanked by the two barcode sequences. The large number of double stranded polynucleotides produced at the end of the barcoding step contains a number of groups of identical polynucleotides, wherein each of the groups of the polynucleotides correspond to one polynucleotide present in the plurality of polynucleotides added to the reaction mixture in the tagging step.

In certain embodiments of the invention, the double stranded polynucleotides produced during the barcoding step are purified.

In the next step of the invention, the double stranded polynucleotides produced in the barcoding step are further PCR amplified using a third primer set comprising a first sequencing primer and a second sequencing primer. During this step, the sequences that are used as binding sequences for the sequencing primers in the paired-end sequence step are incorporated in to the double stranded polynucleotides, and therefore, this step is referred to as "the sequencing primer incorporation step".

As noted above, the first barcode primer comprises a sequence corresponding to a 3' portion of the first sequencing primer; whereas, the second barcode primer comprises a sequence corresponding to a 3' portion of the second sequencing primer. Therefore, during the first PCR cycle of the sequencing primer incorporation step, the 3' ends of the first and the second sequencing primers bind to the corresponding sequences and contain overhangs at the 5' end. At the end of the first PCR cycle of the sequencing primer incorporation step, the overhangs at the 5' ends of the primers are incorporated in to the double stranded polynucleotides. In the subsequent PCR cycles, the entirety of the first and the second sequencing primers bind to the corresponding sequences on the template single strands.

The first and the second sequencing primers have lengths of about ten to 25 nucleotides, about 12 to 20 nucleotides, or about 15 nucleotides.

In a preferred embodiment, about 20 to about 35 PCR cycles are performed in the sequencing primer incorporation step. The conditions appropriate for the PCR cycles during the sequencing primer incorporation step depend on the denaturation temperatures of the primers and the polymerase enzyme used in the sequencing primer incorporation step. Designing the proper conditions for the PCR cycles based on the primer sequences and the polymerase is well known to a person of ordinary skill in the art.

As such, the sequencing primer incorporation step incorporates the sequences necessary for the sequencing of the double stranded polynucleotides.

In one embodiment, the sequencing primer incorporation step is not performed. In this embodiment, the sequences corresponding to the sequencing primers are incorporated in their entireties in the first and the second barcode primers. Therefore, in such embodiments, the first barcode primer comprises, from the 5' end: a sequence corresponding to a first sequencing primer, a first barcode and an inner PCR primer sequence; whereas, the second barcode primer comprises, from the 5' end: a sequence corresponding to a second sequencing primer, a second barcode and a second 5' target sequence. As such, since the sequences for the first and the second sequencing primers are incorporated during the barcoding step, the sequencing primer incorporation step is not necessary.

At the end of the sequencing primer incorporation step or the barcoding step if the sequencing primer incorporation step is not used, double stranded polynucleotides that are suitable for "deep sequencing" are produced. Accordingly, in the following step of the assay of the invention, the double stranded polynucleotides are deep sequenced using appropriate sequencing primers with the paired-end sequencing technology.

The sequencing primers used in the paired-end sequencing step of the invention have sequences corresponding to the sequences of the first and the second sequencing primers.

The term "deep sequencing" used in the invention refers to sequencing a region, for example, the target of interest, multiple times, for example, hundreds or thousands of times. For example, in the current invention, hundreds or thousands of copies of each of the polynucleotides added in the initial reaction mixture in the tagging step are produced during the nested PCR step, the barcoding step and the sequencing primer incorporation step. In the "deep sequencing" step of the invention, the sequences of each of the hundreds or thousands of copies of each of the polynucleotides produced during the barcoding step are sequenced using "paired-end sequencing".

The term "paired-end sequencing" used herein refers to the sequencing technology where both ends of a fragment are sequenced using specific primer binding sites present on each of the ends of the double stranded polynucleotides. Paired-end sequencing generates high-quality sequencing data which is aligned using a computer software program to generate the sequence of the polynucleotide flanked by the two primer binding sites. Sequencing from both ends of a double stranded molecule allows high quality data from both ends of the double stranded molecule because sequencing from only one end of the molecule may cause the sequencing quality to deteriorate as longer sequencing reads are performed.

In the paired-end sequencing step of the invention, the double stranded polynucleotides produced at the end of the sequencing primer incorporation step or the barcoding step if the sequencing primer incorporation step is not used, are sequenced using a first sequencing primer and a second sequencing primer. The sequence of the first sequencing primer corresponds to the first sequencing primer used in the sequencing primer incorporation step or the "first sequencing primer sequence" portion of the first barcode primer used in the barcoding step if the sequencing primer incorporation step is not performed. The sequence of the second sequencing primer corresponds to the second sequencing primer used in the sequencing primer incorporation step or the "second sequencing primer sequence" portion of the second barcode primer used in the barcoding step if the sequencing primer incorporation step is not performed.

The paired-end sequencing technique is well-known in the art. A general description and the principle of paired-end sequencing is provided in Illumina Sequencing Technology, Illumina, Publication No. 770-2007-002, the contents of which are herein incorporated by reference in their entirety.

In one example of the paired-end sequencing, a step of bridge amplification is used as described in the Shendure et al. reference, the contents of which are incorporated herein by reference in their entirety. Another example of paired-end sequencing is also described in the Kozich et al. reference, the contents of which are also incorporated herein in their entirety.

Non-limiting examples of the paired-end sequencing technology are provided by Illumina MiSeq™, Illumina MiSeqDx™ and Illumina MiSeqFGx™. Additional examples of the paired-end sequencing technology that can be used in the assays of the invention are well known in the art and such embodiments are within the purview of the invention.

In one embodiment, the paired-end sequencing step of the invention is carried out using Illumina MiSeq™ technology. In another embodiment, the paired-end sequencing step of the invention is carried out using Illumina MiSeq™ 2×75 bp kit, Illumina MiSeq™ 2×150 bp kit, Illumina MiSeq™ 2×250 bp kit or Illumina MiSeq™ 2×300 kit.

The sequencing data obtained in the paired-end sequencing step of the invention is further analyzed to identify the sequences of each of the polynucleotides added in the reaction mixture during the tagging step of the invention. The analysis of the sequencing data obtained in the paired-end sequencing step of the invention is designed to screen out unreliable sequencing data and gather and further analyze high quality reliable data to identify the sequences of each of the polynucleotides added in the reaction mixture for the tagging step of the invention.

Figure 2:
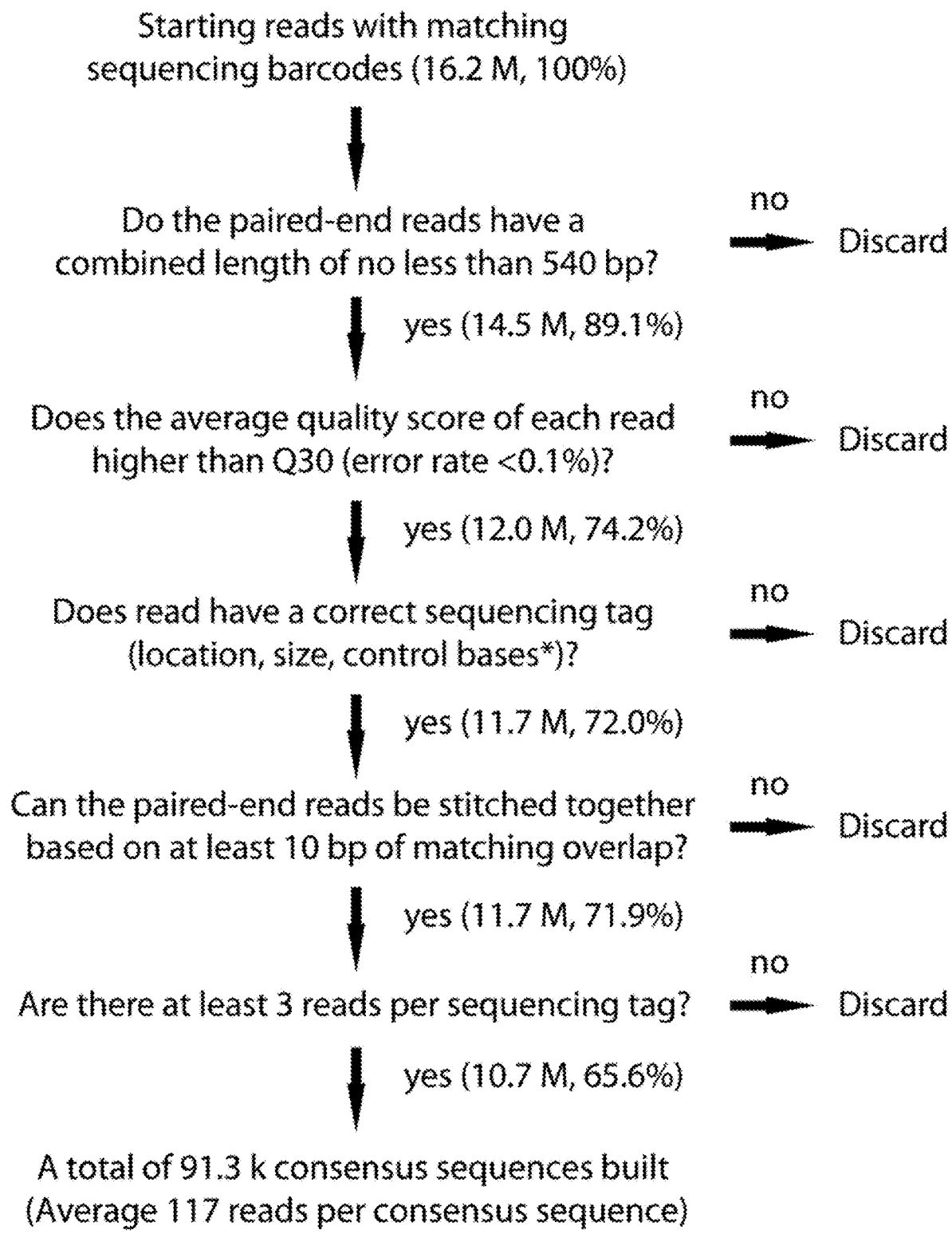
FIG. 2. Workflow for Illumina MiSeq™ paired-end sequence processing and construction of consensus sequences. Raw Illumina MiSeq™ paired-end reads were filtered and stitched using the criteria shown to construct consensus sequences. At each step, reads that did not satisfy the criteria were discarded. Consensus sequences were built based on a minimum of 3 reads that had identical sequence tags. Control bases (asterisk) indicate the 5 non-N, non-binding, degenerate bases, and were used to remove sequences that had sequencing errors. M=million reads; k=thousand reads.

In one embodiment, the sequencing data obtained in the paired-end sequencing step of the invention is analyzed using a computer software program designed to conduct the steps outline in FIG. 2. In one embodiment, the computer software program is designed to remove the sequencing data if the paired-end reads have a combined length of less than the target sequence. For example, if the target sequence is 500 bp in length, the sequencing reads having a combined length of less than about 400 to about 600 or about 500 bp are removed.

In certain embodiments, the computer software is designed to remove the sequencing data if the average quality score for each read is higher than a predetermine error rate, for example, about 0.05% to about 0.2% or about 0.1%. In one embodiment, the sequencing quality score of a given base, Q, is defined by the following equation:

$$Q = -10 \log_{10}(e), \text{ where } e \text{ is the estimated probability of the base call being wrong.}$$

A higher Q scores indicate a smaller probability of error and a lower Q scores can result in a significant portion of the reads being unusable. They may also lead to increased false-positive variant calls, resulting in inaccurate conclusions.

Average quality score for a read indicates the average of the quality scores for all nucleotides in a read.

In a further embodiment, the computer software is designed to remove the sequencing data that do not have accurate sequence, location or size of the unique tag sequence. In an even further embodiment, the computer software is designed to remove the sequencing data if the paired-end reads cannot be stitched together based on at least about 5 bp to about 20 bp or at least about 10 bp of matching overlap sequence.

In yet another embodiment, the computer software is designed to remove the sequencing data if there are less than three sequencing reads for a given unique tag sequence. Having multiple sequences for a given unique tag sequence facilitates identification of sequencing errors where consensus sequences in a number of sequences corresponding a unique tag are determined based on a sequence alignment. Therefore, the mutations that occur in a significant proportion of sequences corresponding to a unique tag sequence are identified as "true mutations", i.e., are identified as mutations present in the polynucleotides added to the reaction mixture during the tagging step of the invention.

An example of the operation of the computer software program according the invention is schematically represented in FIG. 2 and is provided in Example 1.

As such, the invention provides an assay for identifying, from a pool of polynucleotides comprising a target sequence, the polynucleotides that contain a mutation within the target sequence. In certain embodiments, the tagging step, the nested PCR step, the barcoding step, the primer sequence incorporation step and the paired-end sequencing step are carried out by different entities, for example, laboratories or facilities. For example, a first facility/laboratory may perform the tagging step to produce a single stranded complement of a target sequence tagged with the unique tag and outer and inner primer sequences. The single stranded complements so produced can be provided to a second facility/laboratory which can then perform the nested PCR step to amplify the single stranded complement to produce a large number of double stranded copies of the single stranded complement. The double stranded copies so produced can be further provided to a third facility/laboratory which can perform the barcoding step. Further, the resulting product of the barcoding step can be processed in a fourth facility/laboratory according to the sequencing primer incorporation step. Furthermore, the resulting product of the sequencing primer incorporation step can be processed in a fifth facility/laboratory by the paired-end sequencing technology to generate the sequencing data. The sequencing data can be further analyzed by a sixth laboratory/facility.

Further embodiments of the invention also provide kits for carrying out the assay of the invention. The kits of the invention can contain specific primers necessary to carry out the assay of the invention, a computer software program designed to process the sequencing data obtained from the assay and optionally, materials that provide instructions to perform the assay. In one embodiment, the kit of the invention comprises:

a) A plurality of first primers, each of the plurality of the first primers comprising, from the 5' end:

i) an outer PCR primer motif, ii) an inner PCR primer motif, iii) a tag comprising a sequence unique for each of the first primers, wherein the unique sequence comprises about 4-20 nucleotides, and iv) a 3' target sequence which has a sequence that corresponds to the sequence at the 3' end of the target sequence, b) a first primer set comprising:
i) an outer PCR primer having the sequence that corresponds to the outer PCR primer motif portion of the first primer, and
ii) a first 5' target primer having the sequence that corresponds to the sequence at the 5' end of the target sequence, c) a second primer set comprising:
i) a first barcode primer comprising, from the 5' end: a sequence corresponding to a 3' portion of a first sequencing primer, a first barcode and an inner PCR primer sequence, wherein the inner PCR primer sequence corresponds to the inner PCR primer motif portion of the first primer, and
ii) a second barcode primer comprising, from the 5' end: a sequence corresponding to a 3' portion of a second sequencing primer, a second barcode and a second 5' target sequence, wherein the second 5' target sequence corresponds to the portion of the target sequence that is at the 3' end of the sequence corresponding to the first 5' target primer, d) a third primer set comprising:
i) a first sequencing primer having the sequence corresponding to the first paired-end sequencing primer, and
ii) the second sequencing primer having the sequence corresponding to the second paired-end sequencing primer.

The kit of the invention can also further comprise a computer software program designed to process the sequencing data obtained from the assay and optionally, materials that provide instructions to perform the assays of the invention.

In certain embodiments, the kit of the invention can be customized for a specific target sequence. For example, a user may provide the sequence of a target sequence and a kit can be produced to carry out the assay of the invention for the target sequence.

A further embodiment of the invention provides a plurality of primers for producing a single stranded complement of each of a plurality of polynucleotides containing a target sequence, wherein each of the plurality of primers comprises, from the 5' end:
i) an outer PCR primer motif,
ii) an inner PCR primer motif,
iii) a tag comprising a sequence unique for each of the primers, wherein the unique sequence comprises about 4-20 nucleotides, and
iv) a 3' target sequence which has a sequence that corresponds to the sequence at the 3' end of the target sequence.

Various aspects of the outer PCR motif, the inner PCR motif, the tag and the 3' target sequence detailed in the assays of the invention provided above are also applicable to this embodiment of the invention.

An even further embodiment of the invention also provides a method of producing a single stranded complement of each of a plurality of polynucleotides containing a target sequence, the method comprising conducting one cycle of PCR using a plurality of primers, wherein each primer of the plurality of primers comprises, from the 5' end:

i) an outer PCR primer motif,
ii) an inner PCR primer motif,
iii) a tag comprising a sequence unique for each copy of the primer, wherein the unique sequence comprises about 4-20 nucleotides, and
iv) a 3' target sequence which has a sequence that corresponds to the sequence at the 3' end of the target sequence, wherein each of the single stranded complements of each of the plurality of polynucleotides produced in the PCR comprises, from the 5' end:
i) the outer PCR primer motif,
ii) the inner PCR primer motif,
iii) the tag comprising a unique sequence of about 4-20 nucleotides,
iv) the sequence corresponding to the target sequence.

Various aspects of the outer PCR motif, the inner PCR motif, the tag and the 3' target sequence detailed in the assays of the invention provided above are also applicable to this embodiment of the invention. This embodiment of the invention provides the single stranded complements of the plurality of polynucleotides of interest, wherein the single stranded complements can be analyzed further according to the nested PCR step, the barcoding step, the sequencing primer incorporation step and the paired-end sequencing step described above.

Materials and Methods

Viral Samples for Analysis:

HCV RNA was extracted from serum samples using RNA extraction methods, for example, QIAmp Viral RNA kit (Qiagen). cDNA was synthesized using SuperScript III Reverse Transcriptase (Invitrogen) and RT primers that added random sequence tags to cDNA copies of viral RNA templates (FIG. 6). E1E2 and NS3 gene segments were amplified by nested-PCR followed by gel extraction. Pooled DNA library was sequenced on an Illumina MiSeq™ sequencer. Following a Q30 filter that removed low quality reads, a total of 25.7 Gigabases of nucleotides were generated. For each unique sequence tag, a consensus sequence was determined using MAFFT software (see Worldwide Website: mafft.cbrc.jp/alignment/software/), based on an alignment of at least three reads that share the same sequence tag. Nucleotide sequences have been deposited in NCBI SRA under BioProject accession number PRJNA290532.

Study Subjects

Samples from subjects with HIV/HCV co-infection were selected from a repository. Patients were followed per clinical routine and blood samples were collected at regular intervals. HIV and HCV infections were confirmed (anti-HCV; Abbott HCV EIA 2.0 or 3.0 enzyme immunoassay; Abbott Laboratories, Abbott Park, Ill.).

Measurement of HCV RNA Levels

HCV RNA was extracted from serum using a Qiagen Viral RNA Mini column (Qiagen, Valencia, Calif.) following manufacturer's instruction. Viral RNA levels were measured as previously described using quantitative (RT-PCR) assay (Qiagen Quantitect Probe RT-PCR reagent, Valencia, Calif.), except that a modified primer pair was used (Brief Description of Sequences). The AcroMetrix HCV Panel was used as standards (Applied Biosystems by Life Technologies). Amplification products were monitored on a Qiagen Rotor Gene Q Analyzer (Qiagen, Valencia, Calif.).

PCR Amplification and Illumina Sequencing of E1E2 and NS3 Gene Segments

E1E2 and NS3 gene segments were amplified from extracted HCV RNA in separate, independent reactions. A random 12-nucleotide (12-nt) sequence was incorporated in the 5' end of the reverse-transcription (RT) primer to label the initial RNA template during reverse transcription (FIG. 6). This random sequence tag was flanked at the 3' end by the reverse complementary binding site and at the 5' end by the PCR primer binding site. The RT primer for E1E2 region was 5'-TGACTCACGAGTCATCGACTGCAGGCAGAT-NNNNNNNHB-AGCAATAYACYGGGCCACA-3' (SEQ ID NO: 1), where 5'-NNNNNNNBHVHB-3' (nucleotides 31-42 of SEQ ID NO: 1) was the random nucleotide sequence tag to label each viral template. The non-binding degenerate "BHVHB" sequence was designed based on an alignment of 390 subtype 1a HCV reference sequences and the Bole1a HCV sequence. This non-binding strategy was employed to ensure that the random nucleotide sequence tags were not complementary to HCV RNA templates. Similarly, RT primer for the NS3 region was 5'-TGACT-CACGAGTCATCGACTGCAGGCAGATNNNNNNND-DHHHGACCTCATRGTTGTCTCTAG-3' (SEQ ID NO: 2). Following RT reaction, excess RT primers were removed using a Macherey-Nagel DNA purification column (Macherey-Nagel, Bethlehem, Pa., USA), and confirmed using an Agilent 2100 bioanalyzer with picogram sensitivity. A nested-PCR was performed with the reverse primers complementary to the 5' tail of the RT-primer. Sequencing barcodes and sequencing primer binding sites were added during the barcoding step. PCR conditions during the barcoding step were: initial denaturation at 94° C. for 2 min followed by 25 cycles (20 cycles for the $3^{rd}$ PCR) of 94° C. for 20 s, 58° C. for 20 s, and 68° C. for 1 min, an extra 5 min at 68° C. was added at the end of amplification. All primers were designed based on a curated sequence alignment containing 390 non-redundant subtype 1a HCV genomic reference sequences and are listed in the "Brief Description of Sequences".

Final PCR products were purified and quantified using a Qubit kit (Life technologies), and pooled with an equimolar concentration. The concentration of the final DNA pool was quantified by real-time PCR using a SYBR Green qPCR kit (KAPA). The DNA library was then prepped and sequenced on a benchtop MiSeq™ sequencer (Illumina) following manufacturer's instructions. A Q30 filter was used to select high quality reads, resulting in a total of 25.7 Gigabases of nucleotides. Insertions and deletions were found to be minimal in our sequence dataset.

Bioinformatics Analyses

Paired-end sequencing data obtained from Illumina MiSeq™ runs were de-multiplexed into individual samples according to unique combinations of variable-length barcodes at each end. Additional filtering criteria included an exact match to PCR primer sequences, an average quality score of 30 or higher, and a minimum length of 270 bp for each paired-end read. Each paired-end read was joined using FLASh (see: ccb.jhu.edu/software/FLASH/) with a minimum of 10 base overlap. For each sample, joined reads were grouped by unique 12-bp tags that were introduced during reverse transcription. For each unique tag, a consensus sequence was determined based on an alignment of at least three reads using MAFFT (see: mafft.cbrc.jp/alignment/software/). A few consensus sequences that contained base ties at some positions resulting in degenerate bases were excluded from evolution analysis due to software incompatibility. Translation of codons and calculation of resistance-associated mutations were carried out using custom R scripts (see Worldwide Website: r-project.org/) with the BioStrings package see Worldwide Website: //bioconductor.org/packages/release/bioc/html/Biostrings).

BioEdit (version 7.2.5.0; see Worldwide Website: mbio.ncsu.edu/BioEdit/bioedit) was used to visualize sequence reads. Quasispecies complexity was determined by dividing the number of unique variants by the number of total individual variants for a given sample. Quasispecies diversity was determined using within-group p-distance calculated using MEGA (version 6.06; see Worldwide Website: megasoftware.net) and the Maximum Composite Likelihood model. Maximum likelihood trees were built using MEGA. Briefly, the fittest evolutionary model was determined using the integrated ModelTest function in MEGA, followed by tree construction using the General Time Reversible model with Gamma distribution plus invariant sites (GTR+G+I). Phylogeny was tested using bootstrap method with 1000 times of replications. Sliding window analysis was performed using VarPlot (version 1.7, see: sray.med.som.jhmi.edu/SCRoftware/VarPlot) with a window size of 20 codons and a 1 codon increment for each step. Type 1 sequence logos were generated for initial samples using the on-line WebLogo tool (see: weblogo.berkeley.edu/logo.cgi), showing amino acid compositions at each amino acid position in the E2-HVR1 region. Type 2 sequence logos were generated for subsequent samples using VisSPA (version 1.6.6, see: sray.med.som.jhmi.edu/SCRoftware/VisSPA) by querying subsequent consensus sequences against the initial sequences. Only the amino acid residues that changed were shown for type 2 logos, with the height of the logo proportional to the $log_2$ unlikelihood of observing that amino acid at a given position.

Statistical Analysis

Mann-Whitney rank sum test was used to calculate significance of nonsynonymous substitution rates between early versus delayed antiretroviral therapy (ART) groups or between different gene segments; Student's t test was used when normality was satisfied. A paired t test was used to compare the number of drug resistant mutations called by consensus and raw sequences from the same samples. A P value of <0.05 was considered statistical significant.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Identifying Viral Variants in Quasispecies Population

Quantification of accurate proportions of viral variants within viral populations remains a challenge. The assay of the current invention described in this example combines speed and accuracy of the high-throughput MiSeq™ deep sequencing technology with random sequencing tags strategy (FIG. 2) to remove biases and technical artifacts known to obscure true representations of minority variants in a viral quasispecies population. Bioinformatics analyses can be used to automate drug resistance calls to accurately detect minority HIV-1 drug resistance mutations comprising one percent or more of viral quasispecies.

The assay of the invention used for determining viral quasispecies involves isolating the viral RNA from a patient.

The isolated viral RNA was tagged using primers comprising identifying sequences (tags) to amplify the viral RNA and produce tagged cDNA. Tagged cDNA was amplified by PCR, and in-house 2×300 bp paired-end sequencing was performed using a MiSeq™ Benchtop personal sequencer (Illumina). Paired-end reads were then stitched into one complete read using overlapping sequences. This approach generated 10 million reads per run and enabled detection of low abundance viral variants with high sensitivity.

Figure 3:
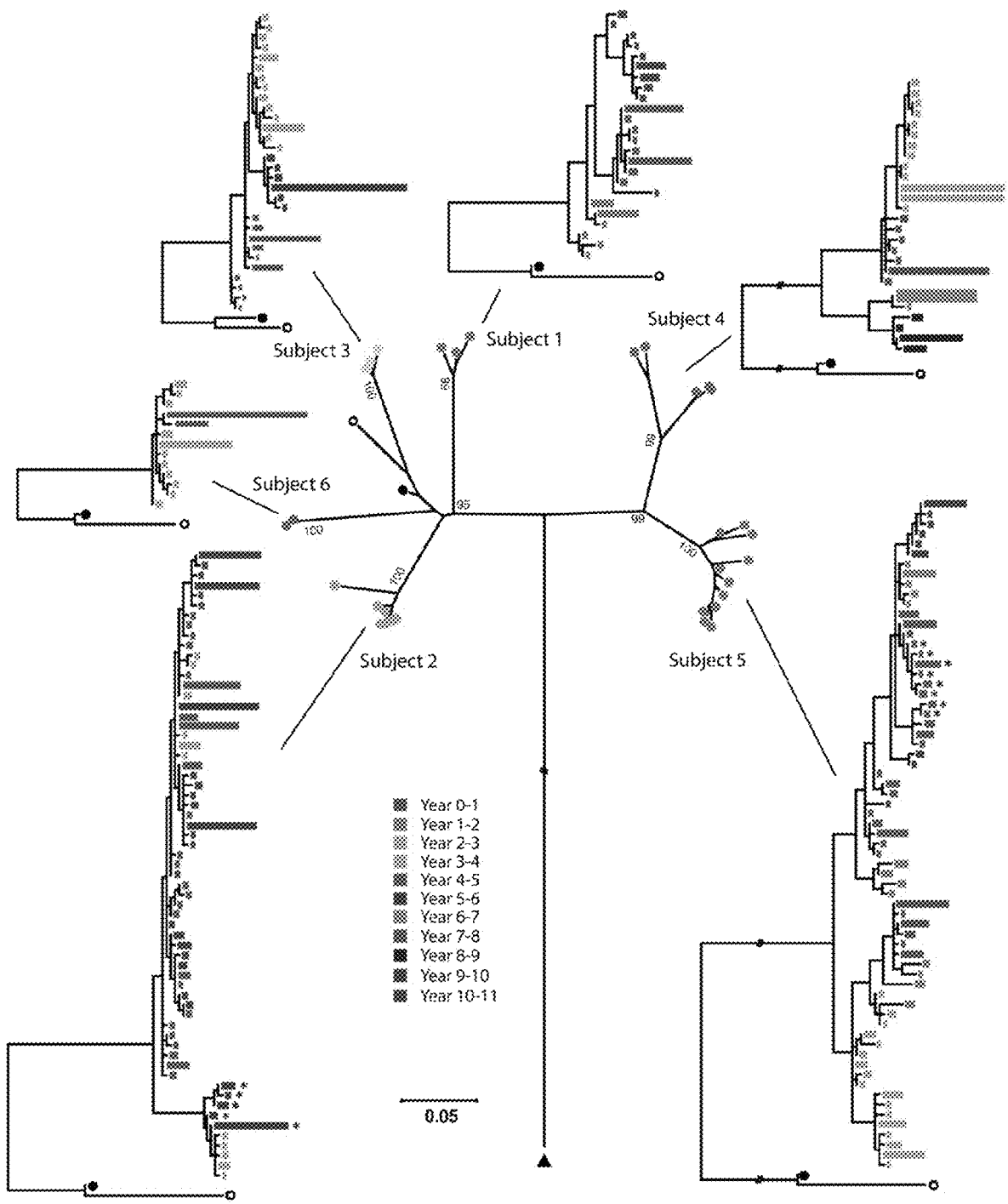
FIG. 3. Phylogenetic analysis revealed temporal evolution of HCV E1E2 quasispecies over 10 years. A master maximum likelihood (ML) tree (center) was built using dominant sequences from each sample. Sequences from the same subject are shown using the same color in the master tree (center). For each subject, detailed maximum likelihood phylogeny of HCV population is shown using representative E1E2 sequences (>=1% in HCV populations). Minority variants (<1% in HCV populations) were excluded for clarity. Longitudinal sequences are indicated by rainbow colors. The length of each horizontal bar indicates the proportion of each variant within the viral population. Highly abundant variants (>80% of the population) are indicated by double bars (e.g. Subject 4, blue bar). When two samples from the same year were available, variants from the later samples are marked with an asterisk (e.g. Subject 2 and 5). Bootstrap values are shown at major nodes in the master tree (center) and are omitted in the individual trees for clarity. Reference sequences are Bole1a (subtype 1a, solid circle, GenBank accession number: JQ791196.1), H77 (subtype 1a, empty circle, GenBank accession number: AF009606) and Con1 (subtype 1b, solid triangle, GenBank accession number: AJ238799). This tree contains sequence information from >16,000 consensus sequences (>50% of all E1E2 consensus sequences) constructed from over 2 million paired-end reads.

Using in vitro transcribed HCV H77c RNA (FIG. 3, top) the assay of the invention is shown to correct nearly all the bias and mis-incorporation/sequencing errors. Comparison of sequences before and after the analysis according to the invention demonstrated that a majority of technical errors were eliminated by the analysis—the background error rate prior to the sequencing correction was $1.53 \times 10^{-3}$ errors per nucleotide (i.e., one error per 15,300 nucleotides), which decreased after the sequencing correction by about 100 fold to $1.41 \times 10^{-5}$ errors per nucleotide (i.e., one error per 141,000 nucleotides). In addition, authentic HCV quasispecies structure in clinical samples was revealed (FIG. 3, bottom). Furthermore, the analysis according to the invention corrected many of the low abundance drug resistant mutations that were erroneously called by the conventional deep sequencing approach (FIG. 4). Thus, the analysis proposed herein effectively improved the sensitivity and accuracy of detection by deep sequencing to below 0.1%.

A 3-member mock RNA community was constructed and transcribed in vitro from plasmid DNA of known HCV sequences (Brief Description of Sequences). RNA concentration was measured by quantitative RTPCR. Variant analysis showed that low frequency variants as low as 0.1-0.2% of the viral population could be detected using the assay of the invention. As such, the assay of the invention is used for quantifying low frequency viral variants with high sensitivity and accuracy in clinical samples.

Four separate amplification assays were developed to interrogate four regions (PR, RT, IN, and ENV) targeted by ART, one amplicon for each region. Subtype B, which is the most prevalent subtype in the Americas, Australia, Japan and Western Europe is used to design PCR primers. A 12-nt random sequence tag was introduced into the reverse-transcription (RT) primer, which tags the starting RNA templates (FIG. 2). This sequence tag is flanked by gene-specific sequence at the 3' end and PCR primer sequence at the 5' end. The random sequence tags are designed so that they are not complementary to HIV-1 viral genome.

To optimize the assay of the invention for HIV-1, control RNA from HIV LAI viral particles was used and RNA was transcribed in vitro from a plasmid DNA containing the HIV LAI sequence. 20,000 copies viral RNA was used as template (measured by quantitative RT-PCR) in a reverse transcription reaction with tagging for cDNA synthesis. Following RT, RNA in hybrid was removed using RNase H treatment, and the synthesized cDNA was purified to remove excess RT primers. The removal of RT was confirmed by Agilent bioanalyzer. RNA removal prevents further incorporation of random sequence tags in subsequent amplification steps. Purified cDNA was then amplified using a nested PCR (FIG. 2), and multiplex barcodes and sequence tails required for paired-end Illumina sequencing were incorporated during the barcoding step.

The sequencing primer incorporation step PCR was performed to add on sequencing primer binding sites. The resulting PCR products were purified, quantified using Qubit, and pooled with equimolar concentration for sequencing. The DNA library was quantified using Kapa Library Quantification kit and subjected to Illumina paired-end sequencing at 2×300 bp on a benchtop MiSeq™ sequencer (Illumina) following manufacturer's instructions.

Following the sequencing step, paired-end reads were filtered and their primer sequences trimmed using a viral sequence analysis. Paired-end reads were stitched together and consensus sequences built based on the unique tags. The resulting population of consensus sequences generated represents the initial population of templates.

A control RNA of known sequence is used to determine and correct for background error rates associated with the first and second rounds of in vitro DNA synthesis. These errors, albeit low, are on the order of 1 mutation in 10,000 bases.

Consensus sequences were aligned, and mutations in the PR, RT, IN and ENV genes associated with ART were interrogated and quantified.

EXAMPLE 2

Sensitivity Testing in Detecting Rare Variants

In vitro transcribed RNA from plasmid DNA that encodes known drug resistance substitutions was used to determine assay sensitivity. RNA concentrations were measured by quantitative RT-PCR. Six mock communities of WT and drug resistant RNA with varying proportions (50%, 10%, 5%, 1%, 0.5%, and 0.1% of drug resistant RNA "spiked" into WT RNA) were constructed. Each mock community was subjected to the assay of the invention in triplicate and sensitivity, specificity and linearity for quantitative detection of drug resistant mutants was determined following the sequence variant analysis.

HIV-1 WT and mutant viral stock (pseudoparticles) were constructed. The amount of p24 viral capsid antigen in the viral stock was determined by enzyme linked immunosorbent assay (ELISA) and viral titers were measured. The mutant viral stock was spiked at varying proportions into WT viral stock. Six different virus mock communities were constructed using the same proportions as the RNA communities. Viral mixtures were normalized by p24 using ELISA and ultra-centrifuged to pellet the virus prior to RNA extraction, reverse transcription, and PCR amplification. The sensitivity, specificity and linearity of the assay using viral stock as the starting material were determined.

This experiment was repeated by spiking the six viral communities into HIV-negative blood. Plasma was separated and viral particles were pelleted. This was followed by the assay of the invention.

EXAMPLE 3

Identifying the HCV Resistant Mutations

The current standard of care for HCV therapy is direct acting agents (DAAs) that target HCV replication. Commercial drug resistance tests are not available to guide HCV therapy. Resistance testing may be particularly relevant for patients who fail DAAs. Therefore, the invention provides a sensitive assay to accurately quantify HCV resistant mutations including minority variants. HCV infects over 180 million individuals worldwide and is the leading cause of liver transplantation due to cirrhosis and hepatocellular carcinoma (HCC). More than 350,000 die annually from liver disease caused by HCV. As DAAs become available worldwide, an increase in the prevalence of HCV drug resistance is expected as patients become more treatment experienced. This example of the invention provides a low cost and sensitive assay for detecting DAA resistant HCV.

$CD4^+$ T-cell depletion from HIV infection leads to a global decline in anti-HCV envelope neutralizing antibody (nAb) response, which may play a role in accelerating liver fibrosis. An increase in anti-HCV nAb titers has been reported during ART. This embodiment of the invention provides the effects of ART on long-term HCV evolution.

HCV quasispecies structure and long-term evolution was studied in HIV/HCV co-infected subjects with ART-induced $CD4^+$ T-cell recovery, and compared to subjects with $CD4^+$ T-cell depletion from delayed ART. The assay of the invention was used to construct authentic viral quasispecies and sequence evolution in HCV envelope, which is the primary target for humoral immune responses, was compared to the evolution of HCV NS3, which is a target for cellular immunity, between the two cohorts.

The assay of the invention corrected biases known to skew the proportions of viral variants, revealing authentic HCV quasispeices structures. Higher rates of HCV envelope sequence evolution in subjects with ART-induced $CD4^+$ T-cell recovery was observed compared to subjects with $CD4^+$ T-cell depletion from delayed ART (p=0.03). Evolutionary rates for NS3 were considerably lower than the rates for envelope (p<0.01), with no significant difference observed between the two groups. Therefore, ART-induced $CD4^+$ T-cell recovery results in rapid sequence evolution in HCV envelope, but not in NS3. These results suggest that suppressive ART disproportionally enhances HCV-specific humoral responses more than cellular responses, resulting in rapid sequence evolution in HCV envelope but not NS3.

Over 35 million people globally are living with HIV and a quarter of these individuals are co-infected with HCV. Compared to HCV mono-infection, HIV co-infection accelerates HCV-related liver fibrosis, cirrhosis, and hepatocellular carcinoma, increasing the overall mortality. With effective ART, liver disease has surpassed AIDS to become a leading cause of hospitalization and death in this co-infected population.

This embodiment of the invention provides the evolution of HCV E1E2 envelope (structural) and NS3 (non-structural) gene segments in HIV/HCV co-infected subjects receiving either early or delayed ART. Significantly higher rates of sequence evolution for HCV envelope was observed in subjects who had early ART and $CD4^+$ T-cell recovery compared to those with progressive $CD4^+$ T-cell depletion due to delayed ART. This difference in evolutionary rates between the two groups was not observed for NS3. Using the methods and the data analyses described in the invention authentic HCV quasispecies were constructed and naturally occurring resistance-associated variants (RAVs), circulating at less than 0.1% of the viral population, were also identified.

Subjects and Samples

Six subjects that had detailed clinical and laboratory data and a sufficient number of samples available were selected. The subjects met the following criteria: (1) HIV and HCV antibody positivity, (2) followed for at least 5 years, (3) received either early ART with $CD4^+$ T-cell recovery of >200 cells/µL between the first and the last samples (referred to as the "early ART" group), or delayed ART with a decline of $CD4^+$ T-cell counts of >200 cells/µL between the first and the last samples (the "delayed ART" group). A total of six subjects were included with three subjects in each group (FIG. 1). The average duration of follow-up was 10.8 years.

HCV Quasispecies Identified at Both Individual and Population Levels

Over 16 million paired-end Illumina reads (over 9 billion bases) were filtered using a set of stringent criteria to remove low-quality reads (FIG. 2). A total of 91,326 (51,099 for E2 and 40,227 for NS3) consensus sequences were generated, averaging 1,054 (range 233 to 5032) consensus sequences per sample from an average of 147,387 (range 26,169 to 328,582) raw reads. Approximately 75% of consensus sequences were formed using 3 to 100 reads, whereas the remaining 25% were built from over 100 reads (maximum 98,124).

Figure 7:
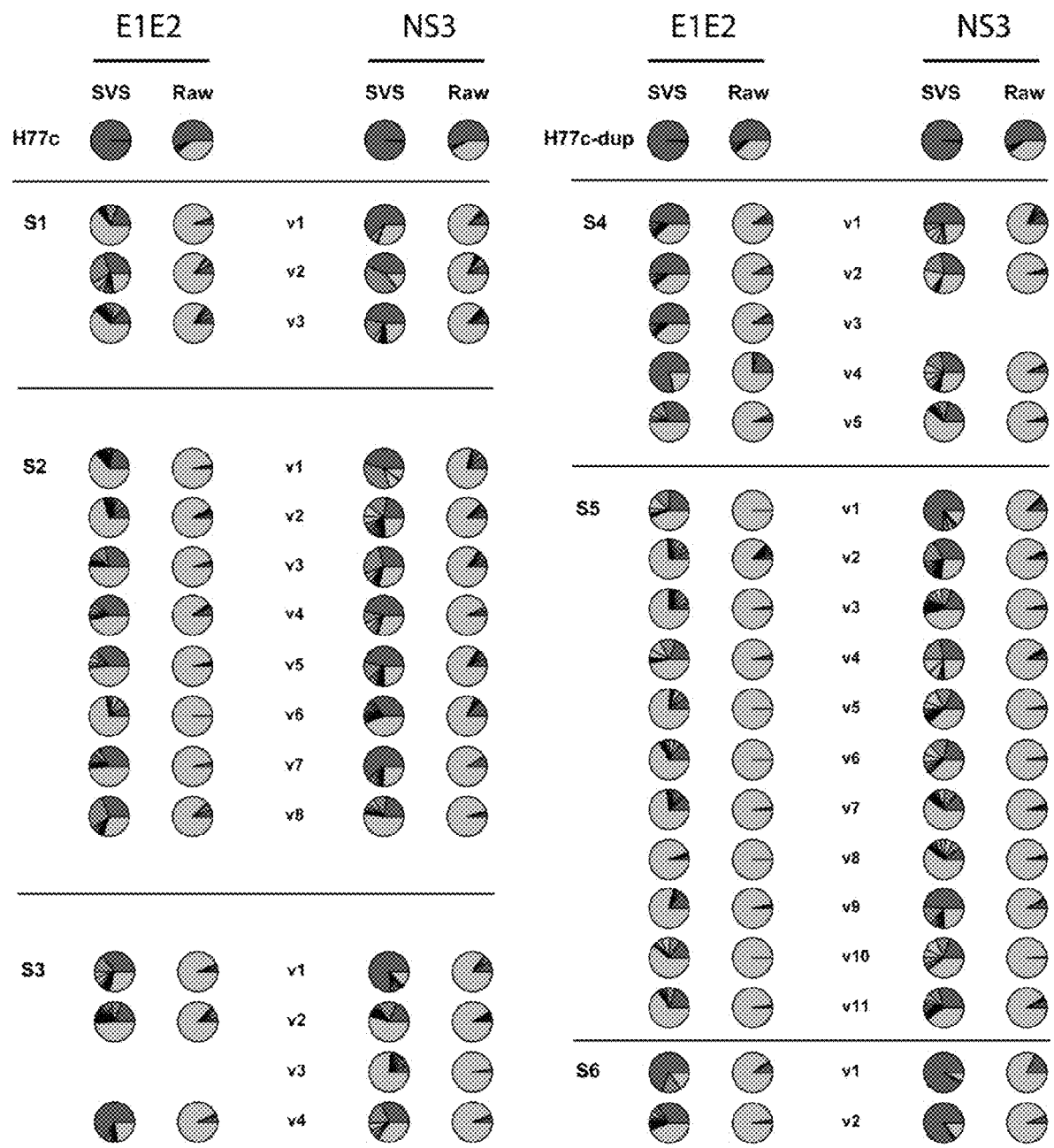
FIG. 7. Identification of authentic structures of HCV quasispecies population. Two regions of the HCV genome were examined (E2 and NS3). Top: RNA transcribed from a control plasmid (H77c). Experiments were performed in duplicates (H77c and H77c-dup). Proportions of unique variants were compared before (Raw) and after the sequencing correction (SVS). Each color represents a unique variant. Rainbow colors representing major (>=1%) variants. Grey represents the sum of all minor variants (<1%). Bottom: longitudinal samples from 6 subjects (S1-S6) with HIV/HCV co-infection. For each subject, 3 to 11 longitudinal samples were analyzed and are shown vertically. V1 represents the earliest time point for each subject. The distribution of sequence variants is shown using grey and rainbow colors in pie charts.

To calculate the background error rate, HCV RNA was synthesized in vitro using a plasmid containing subtype 1a HCV sequence (H77c). E1E2 gene segments containing the hypervariable region 1 (HVR1) and an NS3 gene segment of the in vitro transcript were amplified using the assay of the invention. HCV quasispecies before and after the sequencing correction (FIG. 7, H77c and H77c-dup for duplicate) were compared. Before the sequencing correction, only 55% of raw E1E2 and NS3 sequences were identical to the H77c sequence. After the sequencing correction, 99.38% of E1E2 and NS3 consensus sequences were identical to H77c (99.44% and 98.93% for E1E2 and NS3, respectively). The overall error rate prior to the sequencing correction was $1.53 \times 10^{-3}$ errors per nucleotide (i.e., one error per 15300 nucleotides), which decreased after the sequencing correction by about 100 fold to $1.41 \times 10^{-5}$ errors per nucleotide (i.e., one error per 141,000 nucleotides).

Analysis of clinical samples from HIV/HCV co-infected subjects showed that prior to the sequencing correction (FIG. 7, Raw column), minority variants (defined as <1% of viral population, indicated by color gray) dominated the overall E1E2 and NS3 sequences. Following the sequencing correction (FIG. 7, SVS column), the proportion of minority variants (color gray) was significantly reduced. Thus, the sequencing correction identified the authentic sequences of dominant variants (color red) and unmasked the structure of HCV quasispecies population. Furthermore, in more than half of E1E2 and more than one-third of NS3 amplicons, sequences of dominant variants were different before and after the sequencing correction, indicating that the sequencing correction procedure not only restored the accurate composition of quasispecies but also corrected the technical artifacts that altered the identity of viral sequences.

Figure 8:
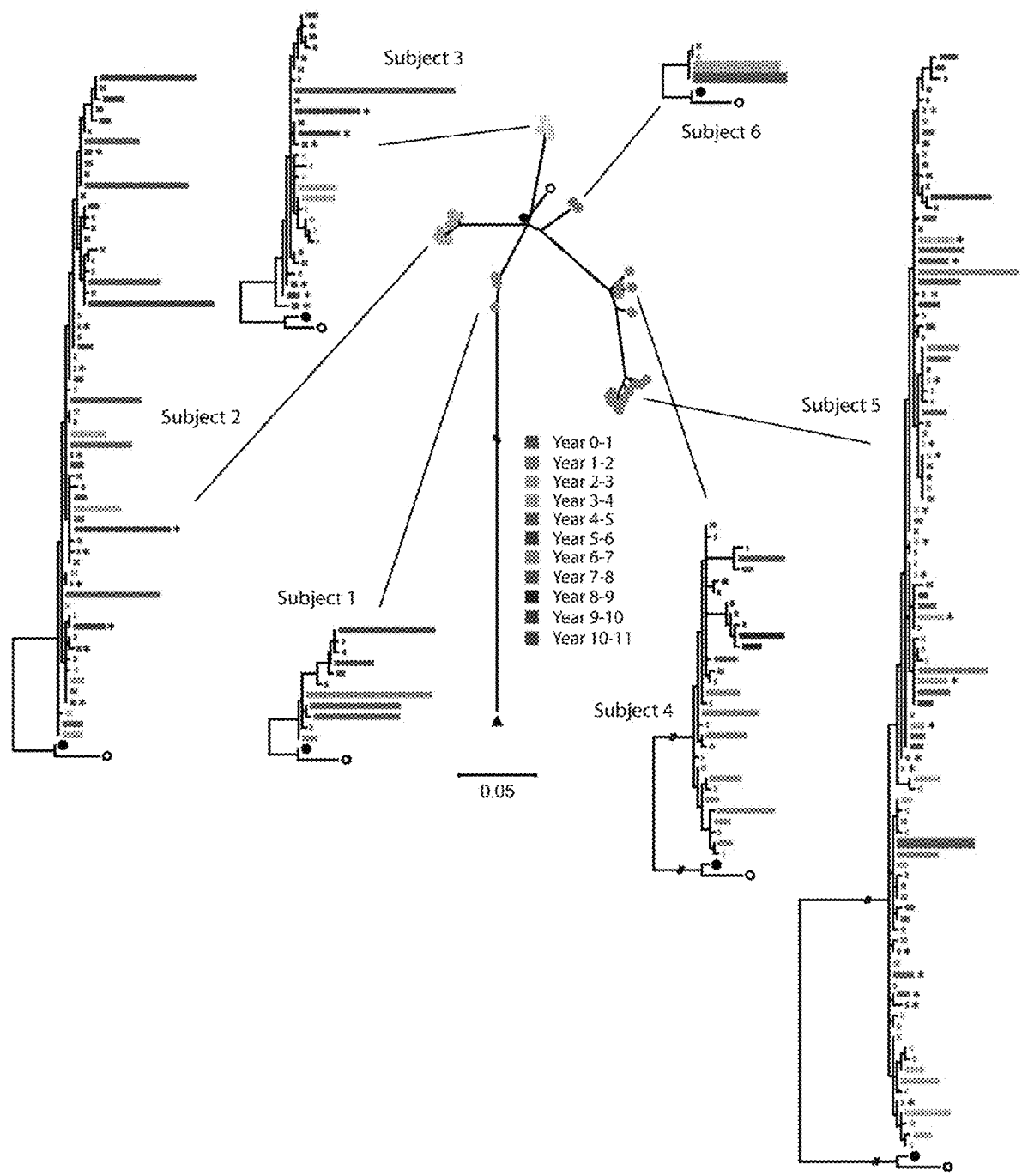
FIG. 8. Phylogenetic analysis of HCV NS3 quasispecies. A master maximum likelihood (ML) tree was built (center) using dominant sequences from each sample. Sequences from the same subject are shown using the same color in the master tree (center). For each subject, detailed maximum likelihood phylogeny of HCV population is shown using representative NS3 sequences (>=1% in HCV populations). Minority variants (<1% in HCV populations) are not shown. Temporal evolution of viral sequences is indicated by the rainbow color. The length of each horizontal color bar indicates the proportion of each variant within the viral population. Highly abundant variants (>80% of the population) are indicated by double bars. When two samples from the same year are depicted, variants from the later samples are marked with an asterisk. Reference sequences are Bole1a (solid circle, GenBank accession number: JQ791196.1), H77 (empty circle, GenBank accession number: AF009606) and Con1 (subtype 1b, solid triangle, GenBank accession number: AJ238799). Over 24,000 consensus sequences (>60% of all NS3 consensus) from ~3 million paired-end reads are represented here.

Distinct Evolutionary Patterns of HCV Quasispecies Between Structural and Non-structural Genes To investigate long-term evolution of HCV quasispecies, the phylogenetic relationship of major sequence variants (defined as >=1% of viral population) was analyzed, which together represents ~60% of all consensus sequences from patient samples (>40,000 sequences). Phylogenies for the structural gene E1E2 envelope (FIG. 3) and the non-structural gene NS3 (FIG. 8) showed different patterns. For E1E2, separate clusters of sequence variants were observed from different time points (FIG. 3, Subject 2 and 5), showing a predominantly temporal order of evolution, i.e. shifting to new clades from one visit to the next. In contrast, many sequence overlaps between visits were observed for NS3 (FIG. 8), consistent with a transitional order of evolution. These differences in evolutionary patterns were more pronounced in subjects 2 and 5, in which more samples were available for analysis. In addition, the envelope sequences showed more diverse major variants (i.e. shorter horizontal bars in E1E2 trees in FIG. 3 and more grey areas in FIG. 7) compared to the variants for NS3. Quasispecies complexity was also significantly higher for E1E2 compared to NS3 (0.44 vs. 0.24 for E1E2 and NS3, respectively, $p=4 \times 10^{-7}$).

Figure 4A:
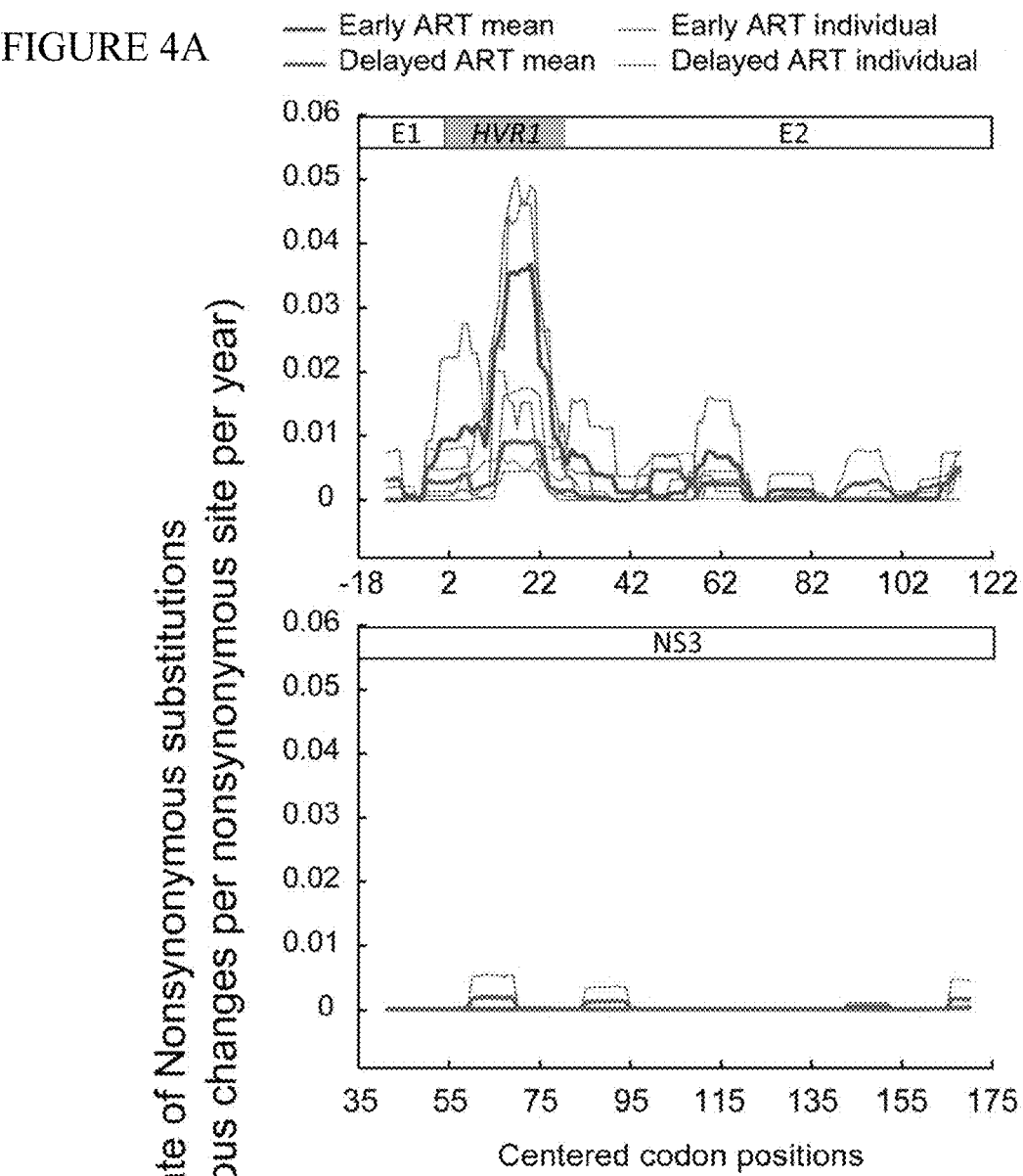
FIGS. 4A-4B. Increased rate of sequence evolution in HCV envelope but not NS3 in subjects with ART-induced CD4+ T-cell recovery. A. Sliding window analysis showing rates of nonsynonymous evolution across E1E2 envelope (upper panel) and NS3 (lower panel) gene segments. Rates of nonsynonymous substitutions were calculated by comparing the first and the last sample of each subject and adjusted by time (interval between visits) using Varplot (Version 1.7, see Materials and Methods). The x-axis indicates the centered codon positions of the respective gene segments. Horizontal bars depict the relative positions in each region in envelope gene segment, i.e. E1, hypervariable region (HVR)-1, and E2. A 10-codon window with 1-codon increment was used. B. Comparison of rates of nonsynonymous evolution between envelope and NS3 gene segments and between early versus delayed ART groups. Rates were calculated by comparing the first and the last sample for each subject using MEGA (Version 6). Mean values are indicated with a short horizontal line in each group. Single-asterisk (*) indicates a P value of <0.05 whereas double-asterisks (**) indicates a p value of less than 0.01. For both A and B, an average of 1,099 consensus sequences per sample were used for the calculation of evolutionary rates.
Figure 4B:
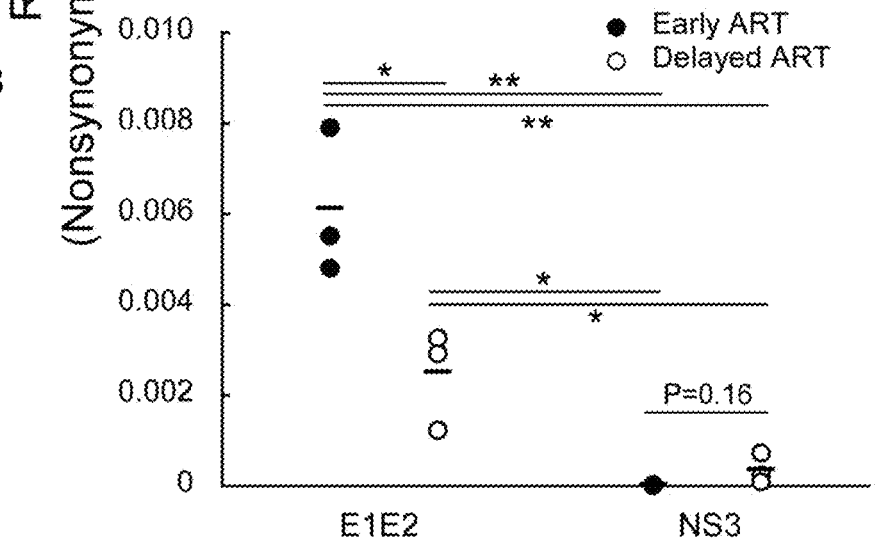

ART-induced CD4+ T-Cell Recovery is Associated with Rapid HCV Envelope Sequence Evolution To evaluate the impact of suppressive ART on HCV quasispecies evolution, the rates of nonsynonymous substitutions between the "early ART" and the "delayed ART" groups were compared (FIG. 4). Envelope sequences showed higher rates of nonsynonymous substitutions than NS3 (average rate of $4.27 \times 10^{-3}$ and $1.80 \times 10^{-4}$ nonsynonymous substitutions per nonsynonymous site per year for E1E2 and NS3 segments, respectively; p<0.01). The "early ART" group had a higher rate of nonsynonymous evolution in HCV envelope compared to the "delayed ART" group (average rate of $6.07 \times 10^{-3}$ and $2.47 \times 10^{-3}$ for early ART and delayed ART, respectively; p=0.03) (FIG. 4B), driven primarily by the more rapid sequence turnover in HVR1 in the early ART group (FIG. 4A, sliding window analysis). In contrast, no significant difference in evolutionary rates for NS3 was found between the two groups (average rate of $2 \times 10^{-5}$ and $3.5 \times 10^{-4}$ for the early and the delayed ART groups, respectively; p=0.16) (FIG. 4B).

Temporal changes were examined in HVR1 amino acid (AA) sequences using high-resolution sequence logo analysis. In the early ART group, HVR1 sequences were replaced sequentially by new sequences. In contrast, HVR1 sequences remained relatively unchanged for 2 of 3 subjects in the delayed ART group. For subject 2, several AA changes in HVR1 sequence occurred at year 5.9, which coincided with an increase in CD4+ T-cell count (from 114 to 553 cells/μL). The AA sequence reverted at year 8 following the decline of CD4+ T-cell from 553 to 278 cells/μL. These data suggest that ART-induced CD4+ T-cell recovery was associated with rapid amino acid sequence evolution in HCV envelope but not in NS3.

Identification of NS3 Resistance-associated Variants in HIV/HCV Co-infection

Figure 5:
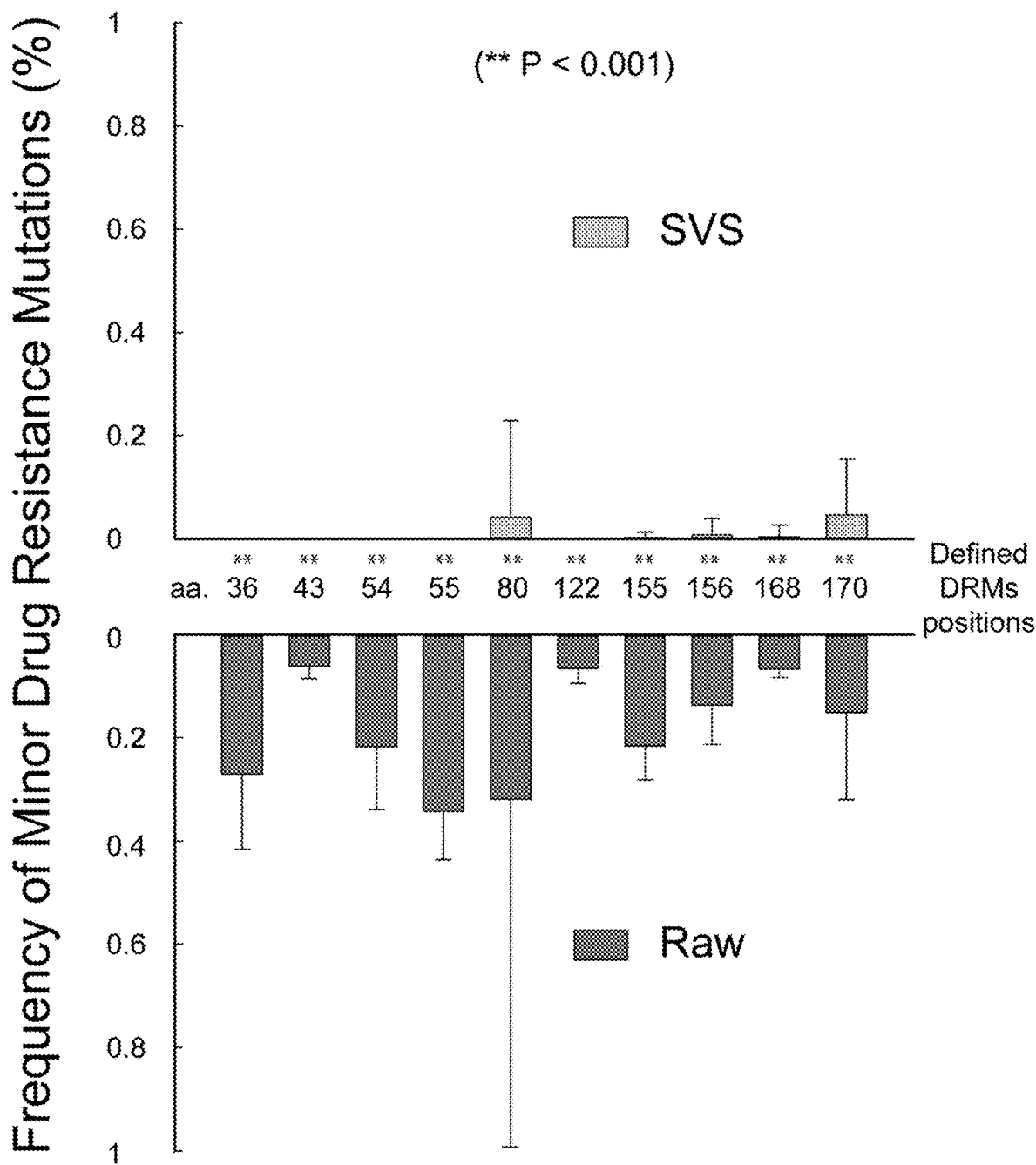
FIG. 5. The sequencing correction significantly reduced the number RAVs erroneously called by conventional deep sequencing. The y-axis indicates the frequency of minor resistance associated variants (RAVs) before (bottom) and after (top) the sequencing correction. The x-axis shows the amino acid (AA) positions of each RAV queried. The height of each bar represents the mean frequency of RAV with standard deviation. Double asterisks indicate a p value <10-32. Dominant NS3 RAVs (FIG. 9, solid symbols with frequency ≥95%) were not included in this analysis.

Naturally occurring NS3 resistance associated variants (RAVs) have been reported for both HCV mono-infected and HIV/HCV co-infected patients. The temporal evolution of authentic NS3 RAVs was quantified. Naturally occurring RAVs were identified in 5 of the 6 subjects (mean detection limit of 0.1%) (FIG. 9). RAV carrying the Q80K mutation was a dominant quasispecies in 3 subjects, and the V55A RAV was dominant in 1 subject. A total of 13 minor RAVs were identified in 5 subjects, all circulating at very low frequencies (0.04-0.86%). Among these, VI170T was found in 7 longitudinal samples from 4 subjects, while each of the remaining minor RAVs was observed in only one subject. Subject 4 had no detectable NS3 RAVs. Overall, 71% (24 of 34) of the samples harbored at least one RAV, of which 53% (18 of 34) had a dominant RAV and 35% (12 of 34) had minor RAVs. The sequencing correction removed over 95% of amino acid substitutions erroneously called as RAVs by the conventional deep sequencing (FIGS. 5 and 9). No significant difference in the number of consensus reads between samples with and without minor RAVs was observed (median 961 vs. 824, P=0.322, n=12 vs. 22).

Application of the Assays of the Invention to Identify HCV Quasispecies

An in-depth analysis of HCV quasispecies evolution in HIV/HCV co-infected subjects followed up to 11 years is presented. ART-induced CD4+ T-cell recovery was shown to be associated with rapid non-synonymous sequence evolution in HCV envelope, and that subjects with CD4+ T-cell depletion and delayed ART had significantly lower rates of HCV envelope evolution. In contrast, the rates of non-synonymous evolution in NS3 were considerably lower compared to HCV envelope with no significant difference between the two groups. These data indicates that ART-induced CD4+ T-cell recovery enhances anti-HCV envelope antibody response, but not anti-HCV cellular response.

Evolution of envelope sequences (especially HVR1) is driven largely by neutralizing antibodies (nAbs). During an acute HCV infection, an early robust nAbs response is associated with rapid envelope sequence evolution and spontaneous clearance of HCV. In patients who progress to chronic infection, nAb responses are delayed but remain persistent, consistent with increasing rates of evolution in the envelope region. Thus, rapid HCV envelope evolution in the early ART group suggests enhanced nAb response upon CD4+ T-cell recovery (FIG. 4). In contrast, lower rates of HCV envelope evolution, particularly with a lack of amino acid changes in the HVR1 for a decade, in the delayed ART group suggest a decline in nAb response from CD4+ T-cell depletion (FIG. 4). Thus, CD4+ T-cell depletion by HIV infection results in a global decline in the anti-HCV nAb response, and that increased nAb titers were observed in patients on suppressive ART.

No difference was observed in the rates of NS3 evolution between the early and the delayed ART groups. Nonsynonymous evolutionary rate in subjects with rising CD4+ T-cell counts approached zero, indicating minimum selective pressure on NS3 over a decade despite CD4+ T-cell recovery. Nonstructural genes such as NS3 are presumably under selective pressure from HCV-specific cellular immune responses that are likely impaired by HCV-induced mechanisms during chronic infection. Given the largely comparable low evolutionary rates among nonstructural genes (p7, NS2-NS5B) during early chronic HCV infection, HIV infection and ART disproportionally affect HCV-specific humoral responses more than cellular responses, resulting in rapid sequence evolution in the envelope but not NS3. ART had little effects on HCV RNA levels or viral clearance, consistent with the findings that rising nAb response alone is insufficient for HCV clearance, unless accompanied by a reversal of T-cell exhaustion. Nonetheless, since HIV co-infection leads to accelerated progression and ART slows the progression of HCV-related liver diseases, this disproportional effect on nAb responses and evolution of HCV envelope suggests a potential protective role of nAbs in HCV liver disease progression.

These results show that co-infected patients who achieved HIV viral suppression with ART had lower rates of hepatic decompensation compared to those who did not maintain HIV suppression. However, despite suppressive ART, co-infected patients continue to have an increased risk of hepatic decompensation compared to HCV-monoinfected individuals, possibly related to ongoing immune dysregulation not reversed by ART. These data are consistent with the current DHHS guideline that recommends initiation of ART among HIV/HCV co-infected patients regardless of CD4+ T cell count, and support the most recent AASLD/IDSA recommendations that prioritize HIV/HCV co-infected individuals for consideration of early HCV therapy to reduce the risk of liver disease progression.

The assays of the invention provide a substantial technical advance in quantifying accurate proportions of dominant and minority variants compared to conventional PCR-based deep sequencing. First, the number of reads that shared the same random sequence tags varied widely (range: 1 to 98,124). This suggests that conventional PCR introduces substantial template re-sampling and PCR amplification bias, and therefore can severely skew the proportions of the initial viral populations if uncorrected. The assays of the invention markedly reduce the effects of PCR bias and template resampling. A large number of nucleotide misincorporation errors, as indicated by the analysis of minority variants (FIG. 7) and resistance-associated variants are also corrected during the data analysis steps of the invention (FIGS. 5 and 9). Strikingly, without the sequencing correction provided by the invention, these artifacts led to incorrect identification of more than half of E1E2 and more than one-third of NS3 dominant variants, highlighting the limitations and the potential risks of conventional clonal or deep sequencing without sequencing correction for technical artifacts. The Illumina workflow obviates the need for homopolymer error correction that frequently complicates the analysis of pyrosequencing data. Furthermore, the low error rate for Illumina minimizes base call errors in the primer tags that could lead to the creation of artificial variants and distort quasispecies distributions. Thus, the assays of the invention allow the determination of viral variants and quasispecies population with high accuracy and sensitivity.

Emergence of RAV is a potential concern for patients receiving DAA therapy. Drug resistance develops rapidly with protease inhibitors monotherapy. This is not surprising because polymorphic RAVs (e.g. V55A, Q80K) and minor RAVs pre-exist in treatment-naïve individuals. In 4 of 6 subjects, HCV populations were dominated by Q80K or V55A over all time points analyzed. In addition, minority RAVs were identified in at least one locus in all but one subject. Among the 10 amino acid sites associated with NS3 resistance, no RAVs were observed in 4 AA sites in any of the samples analyzed (FIG. 9), suggesting that substitutions at these sites may incur a high fitness cost in vivo. Each minority RAV was observed in only one subject, except for IV170T, which was found in 4 of 6 subjects at multiple time points. These results are consistent with the previous data indicating that IV170T has minimal fitness cost compared to wild type HCV. Although SVR rates are high and are comparable between HCV and HIV/HCV co-infection with new DAAs, treatment failure still occurs in a small number of individuals. As such, the invention provides a sensitive and accurate to detect authentic RAVs with minimal bioinformatics or statistical manipulations to correct for technical artifacts.

EXAMPLE 4

Identifying HIV Drug Resistant Mutations

Genotypic assay based on population or bulk sequencing is the most commonly used assay to determine HIV drug resistance mutations. However, because HIV circulates as quasispecies in vivo, current commercial assays are not sensitive in detecting minority drug resistant variants, which are known to compromise clinical response to antiretroviral therapy. An embodiment of the invention provides an accurate and sensitive assay that is capable of detecting drug resistant minority populations and to determine the impact of HIV minor variants on viral suppression to guide rational selection of optimal antiretroviral therapy.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Fettig J, Swaminathan M, Murrill C S, Kaplan J E. Global epidemiology of HIV. *Infect. Dis. Clin. North Am* 2014, 28:323-337.
2. Sherman K E, Rouster S D, Chung R T, Rajicic N. Hepatitis C Virus prevalence among patients infected with Human Immunodeficiency Virus: a cross-sectional analysis of the US adult AIDS Clinical Trials Group. *Clin. Infect. Dis* 2002,34:831-837.
3. Kim A Y, Chung R T. Coinfection with HIV-1 and HCV—a one-two punch. *Gastroenterology* 2009,137: 795-814.
4. Naggie S, Sulkowski M S. Management of patients coinfected with HCV and HIV: a close look at the role for direct-acting antivirals. *Gastroenterology* 2012,142:1324-1334.
5. Bica I, McGovern B, Dhar R, Stone D, McGowan K, Scheib R, et al. Increasing mortality due to end-stage liver disease in patients with human immunodeficiency virus infection. *Clin. Infect. Dis* 2001,32:492-497.
6. Osburn W O, Snider A E, Wells B L, Latanich R, Bailey J R, Thomas D L, et al. Clearance of hepatitis C infection is associated with the early appearance of broad neutralizing antibody responses. *Hepatology* 2014,59:2140-2151.
7. Dowd K A, Netski D M, Wang X H, Cox A L, Ray S C. Selection Pressure from Neutralizing Antibodies Drives Sequence Evolution during Acute Infection with Hepatitis C Virus. *Gastroenterology* 2009,136:2377-2386.
8. Cox A L, Mosbruger T, Mao Q, Liu Z, Wang X H, Yang H C, et al. Cellular immune selection with hepatitis C virus persistence in humans. *J Exp. Med* 2005,201:1741-1752.
9. Netski D M, Mosbruger T, Depla E, Maertens G, Ray S C, Hamilton R G, et al. Humoral immune response in acute hepatitis C virus infection. *Clinical Infectious Diseases* 2005,41:667-675.
10. Villano S A, Vlahov D, Nelson K E, Cohn S, Thomas D L. Persistence of viremia and the importance of long-term follow-up after acute hepatitis C infection. *Hepatology* 1999,29:908-914.
11. McMahan R H, Golden-Mason L, Nishimura M I, McMahon B J, Kemper M, Allen T M, et al. Tim-3 expression on PD-1+ HCV-specific human CTLs is associated with viral persistence, and its blockade restores hepatocyte-directed in vitro cytotoxicity. *J Clin Invest* 2010,120:4546-4557.
12. Rutebemberwa A, Ray S C, Astemborski J, Levine J, Liu L, Dowd K A, et al. High-programmed death-1 levels on hepatitis C virus-specific T cells during acute infection are associated with viral persistence and require preservation of cognate antigen during chronic infection. *J. Immunol* 2008,181:8215-8225.
13. Saito T, Owen D M, Jiang F, Marcotrigiano J, Gale M, Jr. Innate immunity induced by composition-dependent RIG-I recognition of hepatitis C virus RNA. *Nature* 2008,454:523-527.
14. Meylan E, Curran J, Hofmann K, Moradpour D, Binder M, Bartenschlager R, et al. Cardif is an adaptor protein in the RIG-I antiviral pathway and is targeted by hepatitis C virus. *Nature* 2005,437:1167-1172.
15. Raghuraman S, Park H, Osburn W O, Winkelstein E, Edlin B R, Rehermann B. Spontaneous clearance of chronic hepatitis C virus infection is associated with appearance of neutralizing antibodies and reversal of T-cell exhaustion. *J Infect. Dis* 2012,205:763-771.

16. Law M, Maruyama T, Lewis J, Giang E, Tarr A W, Stamataki Z, et al. Broadly neutralizing antibodies protect against hepatitis C virus quasispecies challenge. *Nature Medicine* 2008,14:25-27.

17. Lake-Bakaar G, Dustin L, McKeating J, Newton K, Freeman V, Frost S D. Hepatitis C virus and alanine aminotransferase kinetics following B-lymphocyte depletion with rituximab: evidence for a significant role of humoral immunity in the control of viremia in chronic HCV liver disease. *Blood* 2007,109:845-846.

18. Bjoro K, Froland S S, Yun Z, Samdal H H, Haaland T. Hepatitis C infection in patients with primary hypogammaglobulinemia after treatment with contaminated immune globulin. *N Engl J Med* 1994,331:1607-1611.

19. Osburn W O, Fisher B E, Dowd K A, Urban G, Liu L, Ray S C, et al. Spontaneous Control of Primary Hepatitis C Virus Infection and Immunity Against Persistent Reinfection. *Gastroenterology* 2010,138:315-324.

20. von Hahn T, Yoon J C, Alter H, Rice C M, Rehermann B, Balfe P, et al. Hepatitis C virus continuously escapes from neutralizing antibody and T-cell responses during chronic infection in vivo. *Gastroenterology* 2007,132: 667-678.

21. Farci P, Shimoda A, Wong D, Cabezon T, De Gioannis D, Strazzera A, et al. Prevention of hepatitis C virus infection in chimpanzees by hyperimmune serum against the hypervariable region 1 of the envelope 2 protein. *Proc Natl Acad Sci USA* 1996,93:15394-15399.

22. Feinberg M B. Changing the natural history of HIV disease. *Lancet* 1996,348:239-246.

23. Alimonti J B, Ball T B, Fowke K R. Mechanisms of CD4+T lymphocyte cell death in human immunodeficiency virus infection and AIDS. *J Gen Virol* 2003,84: 1649-1661.

24. Bailey J R, Dowd K A, Snider A E, Osburn W O, Mehta S H, Kirk G D, et al. CD4+ T-Cell-Dependent Reduction in Hepatitis C Virus-Specific Neutralizing Antibody Responses After Coinfection With Human Immunodeficiency Virus. *J Infect Dis* 2015,212:914-923.

25. Lee S, Saraswati H, Yunihastuti E, Gani R, Price P. Patients co-infected with hepatitis C virus (HCV) and human immunodeficiency virus recover genotype cross-reactive neutralising antibodies to HCV during antiretroviral therapy. *Clin Immunol* 2014,155:149-159.

26. Blackard J T, Yang Y, Bordoni P, Sherman K E, Chung R T. Hepatitis C virus (HCV) diversity in HIV-HCV-coinfected subjects initiating highly active antiretroviral therapy. *J Infect. Dis* 2004,189:1472-1481.

27. Qin H, Shire N J, Keenan E D, Rouster S D, Eyster M E, Goedert J J, et al. HCV quasispecies evolution: association with progression to end-stage liver disease in hemophiliacs infected with HCV or HCV/HIV. *Blood* 2005,105:533-541.

28. Liu L, Fisher B E, Dowd K A, Astemborski J, Cox A L, Ray S C. Acceleration of hepatitis C virus envelope evolution in humans is consistent with progressive humoral immune selection during the transition from acute to chronic infection. *J. Virol* 2010,84:5067-5077.

29. Cox A L, Netski D M, Mosbruger T, Sherman S G, Strathdee S, Ompad D, et al. Prospective evaluation of community-acquired acute-phase hepatitis C virus infection. *Clin. Infect. Dis* 2005,40:951-958.

30. Thimme R, Oldach D, Chang K M, Steiger C, Ray S C, Chisari F V. Determinants of viral clearance and persistence during acute hepatitis C virus infection. *J. Exp. Med* 2001,194:1395-1406.

31. *Jabara C B*, Jones C D, Roach J, Anderson J A, Swanstrom R. Accurate sampling and deep sequencing of the HIV-1 protease gene using a Primer ID. *Proc. Natl. Acad. Sci. U.S.A* 2011,108:20166-20171.

32. Jabara C B, Hu F, Mollan K R, Williford S E, Menezes P, Yang Y, et al. Hepatitis C Virus (HCV) NS3 sequence diversity and antiviral resistance-associated variant frequency in HCV/HIV coinfection. *Antimicrob. Agents Chemother* 2014,58:6079-6092.

33. Loman N J, Misra R V, Dallman T J, Constantinidou C, Gharbia S E, Wain J, et al. Performance comparison of benchtop high-throughput sequencing platforms. *Nat Biotechnol* 2012,30:434-439.

34. Wang G P, Sherrill-Mix S A, Chang K M, Quince C, Bushman F D. Hepatitis C virus transmission bottlenecks analyzed by deep sequencing. *J. Virol* 2010,84:6218-6228.

35. Becker E A, Burns C M, Leon E J, Rajabojan S, Friedman R, Friedrich T C, et al. Experimental analysis of sources of error in evolutionary studies based on Roche/454 pyrosequencing of viral genomes. *Genome Biol. Evol* 2012,4:457-465.

36. Kirst M E, Li E C, Wang C X, Dong H J, Liu C, Fried M W, et al. Deep sequencing analysis of HCV NS3 resistance-associated variants and mutation linkage in liver transplant recipients. *PLoS. One* 2013, 8:e69698.

37. Yanagi M, Purcell R H, Emerson S U, Bukh J. Transcripts from a single full-length cDNA clone of hepatitis C virus are infectious when directly transfected into the liver of a chimpanzee. *Proc. Natl. Acad. Sci. U.S.A* 1997,94:8738-8743.

38. Kieffer T L, Sarrazin C, Miller J S, Welker M W, Forestier N, Reesink H W, et al. Telaprevir and pegylated interferon-alpha-2a inhibit wild-type and resistant genotype 1 hepatitis C virus replication in patients. *Hepatology* 2007,46:631-639.

39. Susser S, Welsch C, Wang Y, Zettler M, Domingues F S, Karey U, et al. Characterization of resistance to the protease inhibitor boceprevir in hepatitis C virus-infected patients. *Hepatology* 2009,50:1709-1718.

40. Liu L, Fisher B E, Thomas D L, Cox A L, Ray S C. Spontaneous clearance of primary acute hepatitis C virus infection correlated with high initial viral RNA level and rapid HVR1 evolution. *Hepatology* 2012,55:1684-1691.

41. Bailey J R, Wasilewski L N, Snider A E, El-Diwany R, Osburn W O, Keck Z, et al. Naturally selected hepatitis C virus polymorphisms confer broad neutralizing antibody resistance. *J Clin. Invest* 2015,125:437-447.

42. Bowen D G, Walker C M. Adaptive immune responses in acute and chronic hepatitis C virus infection. *Nature* 2005,436:946-952.

43. Limketkai B N, Mehta S H, Sutcliffe C G, Higgins Y M, Torbenson M S, Brinkley S C, et al. Relationship of liver disease stage and antiviral therapy with liver-related events and death in adults coinfected with HIV/HCV. *JAMA* 2012,308:370-378.

44. Brau N, Salvatore M, Rios-Bedoya C F, Fernandez-Carbia A, Paronetto F, Rodriguez-Orengo J F, et al. Slower fibrosis progression in HIV/HCV-coinfected patients with successful HIV suppression using antiretroviral therapy. *J Hepatol* 2006,44:47-55.

45. Lo Re V, 3rd, Kallan M J, Tate J P, Localio A R, Lim J K, Goetz M B, et al. Hepatic decompensation in antiretroviral-treated patients co-infected with HIV and hepatitis C virus compared with hepatitis C virus-monoinfected patients: a cohort study. *Ann Intern Med* 2014,160:369-379.

46. Panel on Antiretroviral Guidelines for Adults and Adolescents. Guidelines for the use of antiretroviral agents in HIV-1-infected adults and adolescents. Department of Health and Human Services. Available at Worldwide Website: aidsinfo.nih.gov/ContentFiles/AdultandAdolescentGL.pdf.

47. AASLD IDSA HCV Guidance Panel. Hepatitis C guidance: AASLD-IDSA recommendations for testing, managing, and treating adults infected with hepatitis C virus. *Hepatology* 2015,62:932-954.

48. Van den Hoecke S, Verhelst J, Vuylsteke M, Saelens X. Analysis of the genetic diversity of influenza A viruses using next-generation DNA sequencing. *BMC Genomics* 2015,16:79.

49. Bartels D J, Zhou Y, Zhang E Z, Marcial M, Byrn R A, Pfeiffer T, et al. Natural prevalence of hepatitis C virus variants with decreased sensitivity to NS3.4A protease inhibitors in treatment-naive subjects. *J. Infect. Dis* 2008, 198:800-807.

50. Halfon P, Locarnini S. Hepatitis C virus resistance to protease inhibitors. *J Hepatol* 2011,55:192-206.

51. Tong X, Bogen S, Chase R, Girijavallabhan V, Guo Z, Njoroge F G, et al. Characterization of resistance mutations against HCV ketoamide protease inhibitors. *Antiviral Res* 2008,77:177-185.

52. Shimakami T, Welsch C, Yamane D, McGivern D R, Yi M, Zeuzem S, et al. Protease inhibitor-resistant hepatitis C virus mutants with reduced fitness from impaired production of infectious virus. *Gastroenterology* 2011, 140:667-675.

53. Naggie S, Cooper C, Saag M, Workowski K, Ruane P, Towner W J, et al. Ledipasvir and Sofosbuvir for HCV in Patients Coinfected with HIV-1. *N. Engl. J. Med* 2015, 373:705-713.

54. Wyles D L, Ruane P J, Sulkowski M S, Dieterich D, Luetkemeyer A, Morgan T R, et al. Daclatasvir plus Sofosbuvir for HCV in Patients Coinfected with HIV-1. *N. Engl. J. Med* 2015,373:714-725.

55. Munshaw S, Bailey J R, Liu L, Osburn W O, Burke K P, Cox A L, et al. Computational reconstruction of Bole1a, a representative synthetic hepatitis C virus subtype 1a genome. *J. Virol* 2012,86:5915-5921.

56. Lo R V, III, Frank I, Gross R, et al. Self-reported hepatitis B and C virus infections had low sensitivity among HIV-infected patients. J Clin Epidemiol 2007; 60:294-9.

57. Lo R V, III, Wertheimer B, Localio A R, et al. Incidence of transaminitis among HIV-infected patients with occult hepatitis B. J Clin Virol 2008; 43:32-6.

58. DallaPiazza M, Amorosa V K, Localio R, Kostman J R, Lo R V, III. Prevalence and risk factors for significant liver fibrosis among HIV-monoinfected patients. BMC Infect Dis 2010; 10:116.

59. Li Q, Brass A L, Ng A, et al. A genome-wide genetic screen for host factors required for hepatitis C virus propagation. Proc Natl Acad Sci USA 2009; 106:16410-5.

60. Munshaw S, Bailey J R, Liu L, et al. Computational reconstruction of Bole1a, a representative synthetic hepatitis C virus subtype 1a genome. J Virol 2012; 86:5915-21.

61. Liu L, Fisher B E, Dowd K A, Astemborski J, Cox A L, Ray S C. Acceleration of hepatitis C virus envelope evolution in humans is consistent with progressive humoral immune selection during the transition from acute to chronic infection. J Virol 2010; 84:5067-77.

62. Liu L, Fisher B E, Thomas D L, Cox A L, Ray S C. Spontaneous clearance of primary acute hepatitis C virus infection correlated with high initial viral RNA level and rapid HVR1 evolution. Hepatology 2012; 55:1684-91.

63. Chung R T, Andersen J, Volberding P, et al. Peginterferon Alfa-2a plus ribavirin versus interferon alfa-2a plus ribavirin for chronic hepatitis C in HIV-coinfected persons. N Engl J Med 2004; 351:451-9.

64. Torriani F J, Rodriguez-Torres M, Rockstroh J K, et al. Peginterferon Alfa-2a plus ribavirin for chronic hepatitis C virus infection in HIV-infected patients. N Engl J Med 2004; 351:438-50.

65. Naggie S, Cooper C, Saag M, et al. Ledipasvir and Sofosbuvir for HCV in Patients Coinfected with HIV-1. N Engl J Med 2015; 373:705-13.

66. Wyles D L, Ruane P J, Sulkowski M S, et al. Daclatasvir plus Sofosbuvir for HCV in Patients Coinfected with HIV-1. N Engl J Med 2015; 373:714-25.

67. Hepatitis C Guidance: AASLD-IDSA Recommendations for Testing, Managing, and Treating Adults Infected with Hepatitis C Virus. Hepatology 2015.

68. Romano K P, Ali A, Aydin C, et al. The molecular basis of drug resistance against hepatitis C virus NS3/4A protease inhibitors. PLoS Pathog 2012; 8:e1002832.

69. Vallet S, Viron F, Henquell C, et al. NS3 protease polymorphism and natural resistance to protease inhibitors in French patients infected with HCV genotypes 1-5. Antivir Ther 2011; 16:1093-102.

70. Jabara C B, Hu F, Mollan K R, et al. Hepatitis C Virus (HCV) NS3 sequence diversity and antiviral resistance-associated variant frequency in HCV/HIV coinfection. Antimicrob Agents Chemother 2014; 58:6079-92.

71. Shendure et al. (2008), *Nature Biotechnology*, 26, 1135-1145.

72. Illumina Sequencing Technology, Illumina, Publication No. 770-2007-002, available at Worldwide Website: illumina.com/documents/products/techspotlights/techspotlight_sequencing.pdf.

73. Kozich et al. (2013), Applied and Environmental Microbiology, 79(7), p. 5112-5120).

We claim:

1. An assay to identify, from a plurality of polynucleotides, a polynucleotide having a mutation within a target sequence, the assay comprising the steps of:
   a) producing a single-stranded complement of each of the plurality of polynucleotides containing the target sequence by conducting one cycle of PCR using a plurality of first primers, wherein each of the plurality of first primers comprises, from the 5' end:
      i) an outer PCR primer motif,
      ii) an inner PCR primer motif,
      iii) a tag comprising a sequence unique for each of the first primers, wherein the unique sequence comprises about 4-20 nucleotides, and
      iv) a 3' target sequence which has a sequence that hybridizes to the sequence at the 3' end of the target sequence,
   wherein each of the single-stranded complements of each of the plurality of polynucleotides produced in this step comprises, from the 5' end:
      i) the outer PCR primer motif,
      ii) the inner PCR primer motif,
      iii) the tag comprising a unique sequence of about 4-20 nucleotides, and
      iv) the 3' target sequence,
   b) optionally, isolating the single-stranded complements produced in step a),
   c) PCR amplifying the single-stranded complements produced in step a) or isolated in step b) using a first primer set comprising an outer PCR primer and a first 5' target primer to produce multiple double-stranded copies of each of the single-stranded complements produced in step a), wherein the outer PCR primer has a sequence that corresponds to the outer PCR primer motif portion of the first primers and the first 5' target primer has a sequence that corresponds to the sequence at the 5' end of the target sequence, d) optionally, isolating the double-stranded copies produced in step c), e) PCR amplifying the double-stranded copies produced in step c) or isolated in step d) using a second primer set comprising:
   i) a first barcode primer comprising, from the 5' end: a sequence corresponding to a 3' portion of a first sequencing primer, a first barcode and an inner PCR primer sequence, wherein the inner PCR primer sequence corresponds to the inner PCR primer motif portion of the first primer, and
   ii) a second barcode primer comprising, from the 5' end: a sequence corresponding to a 3' portion of a second sequencing primer, a second barcode and a second 5' target sequence, wherein the second 5' target sequence corresponds to the portion of the target sequence that is at the 3' end of the sequence corresponding to the first 5' target primer, f) optionally, isolating the amplified double-stranded copies produced in step e), g) PCR amplifying the double-stranded copies produced in step e) or isolated in step f) using a third primer set comprising a first sequencing primer and a second sequencing primer, wherein the first sequencing primer has a sequence corresponding to a first paired-end sequencing primer and the second sequencing primer has a sequence corresponding to a second paired-end sequencing primer, h) optionally, isolating the amplified double-stranded copies produced in step g), and i) subjecting the double-stranded copies produced in step g) or isolated in step h) to paired-end sequencing using the first paired-end sequencing primer and the second paired-end sequencing primer.

2. The assay of claim 1, wherein the target sequence is a gene of interest and the plurality of polynucleotides is a sample of polynucleotides obtained from a subject.

3. The assay of claim 2, wherein the gene of interest is a drug-resistant gene of an RNA virus and the sample of polynucleotides obtained from the subject is a viral RNA sample from the subject.

4. The assay of claim 3, wherein the RNA virus is human immunodeficiency virus or hepatitis C virus.

5. The assay of claim 1, wherein the target sequence is an mRNA of interest and the plurality of polynucleotides is a sample of mRNA obtained from a subject.

6. The assay of claim 5, wherein the mRNA of interest encodes an oncogenic protein of interest and the sample of mRNA is obtained from a tumor from the subject.

7. The assay of claim 1, wherein the tag is about 12 nucleotides in length.

8. The assay of claim 1, wherein each of the outer PCR primer motif, the inner PCR primer motif, the 3' target sequence, the outer PCR primer sequence, the first 5' target primer, the inner PCR primer sequence, the sequence corresponding to the 3' portion of the first sequencing primer, the sequence corresponding to the 3' portion of the second sequencing primer, the first sequencing primer, and the second sequencing primer are each about 15 nucleotides in length.

9. The assay of claim 1, wherein the first and the second barcodes are four to eight nucleotides in length.

10. The assay of claim 1, wherein the isolating in steps d), f) and h) is performed by gel extraction.

* * * * *

UNITED STATES PATENT AND TRADEMARK OFFICE
CERTIFICATE OF CORRECTION

PATENT NO.        : 10,815,523 B2
APPLICATION NO.   : 16/067191
DATED             : October 27, 2020
INVENTOR(S)       : Wang et al.

Page 1 of 1

It is certified that error appears in the above-identified patent and that said Letters Patent is hereby corrected as shown below:

In the Specification

Column 6,
Line 14, SEQ ID NO: 1, "AGGCAGATNNNNNNNHVHBA" should read --AGGCAGATNNNNNNNBHVHBA--.
Line 19, SEQ ID NO: 2, "AGGCAGATNNNNNNNDHHHG" should read --AGGCAGATNNNNNNNDDHHHG--.

Column 25,
Lines 7-8, "5'-TGACTCACGAGTCATCGACTGCAGGCAGATNNNNNNNHB-AGCAATAYACYGGGCCACA-3'" should read --5'-TGACTCACGAGTCATCGACTGCAGGCAGATNNNNNNNBHVHB-AGCAATAYACYGGGCCACA-3'--.

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 44

<210> SEQ ID NO 1
<211> LENGTH: 61
<212> TYPE: DNA
<213> ORGANISM: Artificial Sequence
<220> FEATURE:
<223> OTHER INFORMATION: primer
<220> FEATURE:
<221> NAME/KEY: misc_feature
```

```
<222> LOCATION: (31)..(37)
<223> OTHER INFORMATION: n is a, c, g, or t

<400> SEQUENCE: 1
tgactcacga gtcatcgact gcaggcagat nnnnnnnbhv hbagcaatay acygggccac    60
a                                                                   61

<210> SEQ ID NO 2
<211> LENGTH: 62
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (31)..(37)
<223> OTHER INFORMATION: n is a, c, g, or t

<400> SEQUENCE: 2
tgactcacga gtcatcgact gcaggcagat nnnnnnnddh hhgacctcat rgttgtctct    60
ag                                                                  62

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
atggcatggg atatgatgat gaact                                         25

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
atyacrgcrt aygcccagca                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tgactcacga gtcatcgact                                               20

<210> SEQ ID NO 6
<211> LENGTH: 52
<212> TYPE: DNA
<213> ORGANISM: Artificial Sequence
<220> FEATURE:
<223> OTHER INFORMATION: primer

<400> SEQUENCE: 6
ctacacgacg ctcttccgat ctcgtgtaca gcatrgcgta yttytccatg gt           52

<210> SEQ ID NO 7
<211> LENGTH: 52
<212> TYPE: DNA
```

<213> ORGANISM: Artificial Sequence
<220> FEATURE:
<223> OTHER INFORMATION: primer

<400> SEQUENCE: 7
ctacacgacg ctcttccgat cttgactgac gcatrgcgta yttytccatg gt        52

<210> SEQ ID NO 8
<211> LENGTH: 51
<212> TYPE: DNA
<213> ORGANISM: Artificial Sequence
<220> FEATURE:
<223> OTHER INFORMATION: primer

<400> SEQUENCE: 8
ctacacgacg ctcttccgat ctctagctag catrgcgtay ttytccatgg t          51

<210> SEQ ID NO 9
<211> LENGTH: 51
<212> TYPE: DNA
<213> ORGANISM: Artificial Sequence
<220> FEATURE:
<223> OTHER INFORMATION: primer

<400> SEQUENCE: 9
ctacacgacg ctcttccgat ctactgtcag catrgcgtay ttytccatgg t          51

<210> SEQ ID NO 10
<211> LENGTH: 50
<212> TYPE: DNA
<213> ORGANISM: Artificial Sequence
<220> FEATURE:
<223> OTHER INFORMATION: primer

<400> SEQUENCE: 10
ctacacgacg ctcttccgat ctgtagtggc atrgcgtayt tytccatggt            50

<210> SEQ ID NO 11
<211> LENGTH: 50
<212> TYPE: DNA
<213> ORGANISM: Artificial Sequence
<220> FEATURE:
<223> OTHER INFORMATION: primer

<400> SEQUENCE: 11
ctacacgacg ctcttccgat ctcatgcggc atrgcgtayt tytccatggt            50

<210> SEQ ID NO 12
<211> LENGTH: 49
<212> TYPE: DNA
<213> ORGANISM: Artificial Sequence
<220> FEATURE:
<223> OTHER INFORMATION: primer

<400> SEQUENCE: 12
ctacacgacg ctcttccgat ctgcagtgca trgcgtaytt ytccatggt             49

<210> SEQ ID NO 13
<211> LENGTH: 49
<212> TYPE: DNA
<213> ORGANISM: Artificial Sequence
<220> FEATURE:
<223> OTHER INFORMATION: primer

<400> SEQUENCE: 13
ctacacgacg ctcttccgat cttagctgca trgcgtaytt ytccatggt             49

<210> SEQ ID NO 14
<211> LENGTH: 48
<212> TYPE: DNA
<213> ORGANISM: Artificial Sequence
<220> FEATURE:
<223> OTHER INFORMATION: primer

<400> SEQUENCE: 14
ctacacgacg ctcttccgat ctagtagcat rgcgtaytty tccatggt                48

<210> SEQ ID NO 15
<211> LENGTH: 50
<212> TYPE: DNA
<213> ORGANISM: Artificial Sequence
<220> FEATURE:
<223> OTHER INFORMATION: primer

<400> SEQUENCE: 15
ctacacgacg ctcttccgat ctcgtgatga gtggagggyg aggtycagat              50

<210> SEQ ID NO 16
<211> LENGTH: 50
<212> TYPE: DNA
<213> ORGANISM: Artificial Sequence
<220> FEATURE:
<223> OTHER INFORMATION: primer

<400> SEQUENCE: 16
ctacacgacg ctcttccgat ctacatcgtg gtggagggyg aggtycagat              50

<210> SEQ ID NO 17
<211> LENGTH: 49
<212> TYPE: DNA
<213> ORGANISM: Artificial Sequence
<220> FEATURE:
<223> OTHER INFORMATION: primer

<400> SEQUENCE: 17
ctacacgacg ctcttccgat ctgcctaagg tggagggyga ggtycagat               49

<210> SEQ ID NO 18
<211> LENGTH: 49
<212> TYPE: DNA
<213> ORGANISM: Artificial Sequence
<220> FEATURE:
<223> OTHER INFORMATION: primer

<400> SEQUENCE: 18
ctacacgacg ctcttccgat cttggtcacg tggagggyga ggtycagat               49

<210> SEQ ID NO 19
<211> LENGTH: 48
<212> TYPE: DNA
<213> ORGANISM: Artificial Sequence
<220> FEATURE:
<223> OTHER INFORMATION: primer

<400> SEQUENCE: 19
ctacacgacg ctcttccgat ctgactgtgt ggagggygag gtycagat                48

<210> SEQ ID NO 20
<211> LENGTH: 48
<212> TYPE: DNA
<213> ORGANISM: Artificial Sequence
<220> FEATURE:

<223> OTHER INFORMATION: primer

<400> SEQUENCE: 20
ctacacgacg ctcttccgat ctcactgtgt ggagggygag gtycagat                48

<210> SEQ ID NO 21
<211> LENGTH: 47
<212> TYPE: DNA
<213> ORGANISM: Artificial Sequence
<220> FEATURE:
<223> OTHER INFORMATION: primer

<400> SEQUENCE: 21
ctacacgacg ctcttccgat ctagtgagtg gagggygagg tycagat                47

<210> SEQ ID NO 22
<211> LENGTH: 47
<212> TYPE: DNA
<213> ORGANISM: Artificial Sequence
<220> FEATURE:
<223> OTHER INFORMATION: primer

<400> SEQUENCE: 22
ctacacgacg ctcttccgat cttcaaggtg gagggygagg tycagat                47

<210> SEQ ID NO 23
<211> LENGTH: 46
<212> TYPE: DNA
<213> ORGANISM: Artificial Sequence
<220> FEATURE:
<223> OTHER INFORMATION: primer

<400> SEQUENCE: 23
ctacacgacg ctcttccgat cttcatgtgg agggygaggt ycagat                 46

<210> SEQ ID NO 24
<211> LENGTH: 48
<212> TYPE: DNA
<213> ORGANISM: Artificial Sequence
<220> FEATURE:
<223> OTHER INFORMATION: primer

<400> SEQUENCE: 24
tgctgaaccg ctcttccgat ctgtcagcat catcgactgc aggcagat               48

<210> SEQ ID NO 25
<211> LENGTH: 48
<212> TYPE: DNA
<213> ORGANISM: Artificial Sequence
<220> FEATURE:
<223> OTHER INFORMATION: primer

<400> SEQUENCE: 25
tgctgaaccg ctcttccgat cttagtcacg catcgactgc aggcagat               48

<210> SEQ ID NO 26
<211> LENGTH: 48
<212> TYPE: DNA
<213> ORGANISM: Artificial Sequence
<220> FEATURE:
<223> OTHER INFORMATION: primer

<400> SEQUENCE: 26
tgctgaaccg ctcttccgat ctacgagtgc catcgactgc aggcagat               48

```
<210> SEQ ID NO 27
<211> LENGTH: 48
<212> TYPE: DNA
<213> ORGANISM: Artificial Sequence
<220> FEATURE:
<223> OTHER INFORMATION: primer

<400> SEQUENCE: 27
tgctgaaccg ctcttccgat ctgaccactt catcgactgc aggcagat                    48

<210> SEQ ID NO 28
<211> LENGTH: 47
<212> TYPE: DNA
<213> ORGANISM: Artificial Sequence
<220> FEATURE:
<223> OTHER INFORMATION: primer

<400> SEQUENCE: 28
tgctgaaccg ctcttccgat ctcagagctc atcgactgca ggcagat                     47

<210> SEQ ID NO 29
<211> LENGTH: 47
<212> TYPE: DNA
<213> ORGANISM: Artificial Sequence
<220> FEATURE:
<223> OTHER INFORMATION: primer

<400> SEQUENCE: 29
tgctgaaccg ctcttccgat ctagcatgtc atcgactgca ggcagat                     47

<210> SEQ ID NO 30
<211> LENGTH: 47
<212> TYPE: DNA
<213> ORGANISM: Artificial Sequence
<220> FEATURE:
<223> OTHER INFORMATION: primer

<400> SEQUENCE: 30
tgctgaaccg ctcttccgat cttatcgtgc atcgactgca ggcagat                     47

<210> SEQ ID NO 31
<211> LENGTH: 47
<212> TYPE: DNA
<213> ORGANISM: Artificial Sequence
<220> FEATURE:
<223> OTHER INFORMATION: primer

<400> SEQUENCE: 31
tgctgaaccg ctcttccgat ctgtacatcc atcgactgca ggcagat                     47

<210> SEQ ID NO 32
<211> LENGTH: 46
<212> TYPE: DNA
<213> ORGANISM: Artificial Sequence
<220> FEATURE:
<223> OTHER INFORMATION: primer

<400> SEQUENCE: 32
tgctgaaccg ctcttccgat ctattggcca tcgactgcag gcagat                      46

<210> SEQ ID NO 33
<211> LENGTH: 46
<212> TYPE: DNA
<213> ORGANISM: Artificial Sequence
<220> FEATURE:
<223> OTHER INFORMATION: primer
```

```
<400> SEQUENCE: 33
tgctgaaccg ctcttccgat ctgatctgca tcgactgcag gcagat          46

<210> SEQ ID NO 34
<211> LENGTH: 46
<212> TYPE: DNA
<213> ORGANISM: Artificial Sequence
<220> FEATURE:
<223> OTHER INFORMATION: primer

<400> SEQUENCE: 34
tgctgaaccg ctcttccgat ctcgacaaca tcgactgcag gcagat          46

<210> SEQ ID NO 35
<211> LENGTH: 46
<212> TYPE: DNA
<213> ORGANISM: Artificial Sequence
<220> FEATURE:
<223> OTHER INFORMATION: primer

<400> SEQUENCE: 35
tgctgaaccg ctcttccgat cttcgataca tcgactgcag gcagat          46

<210> SEQ ID NO 36
<211> LENGTH: 45
<212> TYPE: DNA
<213> ORGANISM: Artificial Sequence
<220> FEATURE:
<223> OTHER INFORMATION: primer

<400> SEQUENCE: 36
tgctgaaccg ctcttccgat ctctgatcat cgactgcagg cagat           45

<210> SEQ ID NO 37
<211> LENGTH: 45
<212> TYPE: DNA
<213> ORGANISM: Artificial Sequence
<220> FEATURE:
<223> OTHER INFORMATION: primer

<400> SEQUENCE: 37
tgctgaaccg ctcttccgat ctgtacgcat cgactgcagg cagat           45

<210> SEQ ID NO 38
<211> LENGTH: 44
<212> TYPE: DNA
<213> ORGANISM: Artificial Sequence
<220> FEATURE:
<223> OTHER INFORMATION: primer

<400> SEQUENCE: 38
tgctgaaccg ctcttccgat ctaagccatc gactgcaggc agat            44

<210> SEQ ID NO 39
<211> LENGTH: 44
<212> TYPE: DNA
<213> ORGANISM: Artificial Sequence
<220> FEATURE:
<223> OTHER INFORMATION: primer

<400> SEQUENCE: 39
tgctgaaccg ctcttccgat cttacccatc gactgcaggc agat            44

<210> SEQ ID NO 40
<211> LENGTH: 44
```

```
<212> TYPE: DNA
<213> ORGANISM: Artificial Sequence
<220> FEATURE:
<223> OTHER INFORMATION: primer

<400> SEQUENCE: 40
tgctgaaccg ctcttccgat ctgtctcatc gactgcaggc agat              44

<210> SEQ ID NO 41
<211> LENGTH: 44
<212> TYPE: DNA
<213> ORGANISM: Artificial Sequence
<220> FEATURE:
<223> OTHER INFORMATION: primer

<400> SEQUENCE: 41
tgctgaaccg ctcttccgat ctctaccatc gactgcaggc agat              44

<210> SEQ ID NO 42
<211> LENGTH: 58
<212> TYPE: DNA
<213> ORGANISM: Artificial Sequence
<220> FEATURE:
<223> OTHER INFORMATION: primer

<400> SEQUENCE: 42
aatgatacgg cgaccaccga gatctacact ctttccctac acgacgctct tccgatct    58

<210> SEQ ID NO 43
<211> LENGTH: 61
<212> TYPE: DNA
<213> ORGANISM: Artificial Sequence
<220> FEATURE:
<223> OTHER INFORMATION: primer

<400> SEQUENCE: 43
caagcagaag acggcatacg agatcggtct cggcattcct gctgaaccgc tcttccgatc   60
t                                                                  61

<210> SEQ ID NO 44
<211> LENGTH: 13
<212> TYPE: DNA
<213> ORGANISM: Artificial Sequence
<220> FEATURE:
<223> OTHER INFORMATION: primer

<400> SEQUENCE: 44
ctgacgacct acg                                                13
```